United States Patent
Li et al.

(10) Patent No.: US 12,201,643 B2
(45) Date of Patent: Jan. 21, 2025

(54) MECHANOCHEMICAL DYNAMIC FOR FOCAL CANCER TREATMENT

(71) Applicant: THE BOARD OF TRUSTEES OF THE UNIVERSITY OF ILLINOIS, Urbana, IL (US)

(72) Inventors: King C. Li, Urbana, IL (US); Gun Kim, Urbana, IL (US); Qiong Wu, Urbana, IL (US); Jeffrey S. Moore, Savoy, IL (US); Yun-Sheng Chen, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 17/965,908

(22) Filed: Oct. 14, 2022

(65) Prior Publication Data

US 2023/0119684 A1   Apr. 20, 2023

Related U.S. Application Data

(60) Provisional application No. 63/256,239, filed on Oct. 15, 2021.

(51) Int. Cl.
| | |
|---|---|
| A61K 31/655 | (2006.01) |
| A61K 9/06 | (2006.01) |
| A61K 31/10 | (2006.01) |
| A61K 31/327 | (2006.01) |
| A61K 47/10 | (2017.01) |
| A61K 47/34 | (2017.01) |
| A61P 35/00 | (2006.01) |

(52) U.S. Cl.
CPC .............. *A61K 31/655* (2013.01); *A61K 9/06* (2013.01); *A61K 31/10* (2013.01); *A61K 31/327* (2013.01); *A61K 47/10* (2013.01); *A61K 47/34* (2013.01); *A61P 35/00* (2018.01)

(58) Field of Classification Search
CPC ........ A61K 31/655; A61K 9/06; A61K 31/10; A61K 31/327; A61K 47/10; A61K 47/34; A61P 35/00
See application file for complete search history.

(56) References Cited

U.S. PATENT DOCUMENTS

| | | | |
|---|---|---|---|
| 5,543,158 A | 8/1996 | Gref et al. | |
| 5,792,742 A | 8/1998 | Gold et al. | |
| 6,007,499 A | * 12/1999 | Martin | ................ A61B 8/4461 601/3 |
| 8,815,771 B2 | 8/2014 | Chopra et al. | |
| 9,687,553 B2 | 6/2017 | Almutairi et al. | |

(Continued)

FOREIGN PATENT DOCUMENTS

| | | | |
|---|---|---|---|
| CN | 111378178 A | * | 7/2020 |
| WO | 2009051837 A2 | | 4/2009 |

(Continued)

OTHER PUBLICATIONS

CN-111378178-A Machine translation (Year: 2020).*

(Continued)

*Primary Examiner* — Matthew P Coughlin
*Assistant Examiner* — Ashli Ariana Chicks
(74) *Attorney, Agent, or Firm* — Lathrop GPM LLP; Lisa Hillman

(57) ABSTRACT

Provided herein are compositions and methods for mechanochemical dynamic therapy.

20 Claims, 19 Drawing Sheets

(56) References Cited

U.S. PATENT DOCUMENTS

| | | |
|---|---|---|
| 9,943,606 B2 | 4/2018 | Lee et al. |
| 10,143,660 B2 | 12/2018 | Nel et al. |
| 10,343,903 B2 | 7/2019 | Zink et al. |
| 10,525,023 B2 | 1/2020 | Jermy et al. |
| 10,583,199 B2 | 3/2020 | Henkin et al. |
| 10,905,653 B2 | 2/2021 | Wang et al. |
| 10,947,350 B2 | 3/2021 | Luo et al. |
| 10,967,003 B2 | 4/2021 | Luo et al. |
| 11,096,911 B2 | 8/2021 | Jermy et al. |
| 11,103,594 B2 | 8/2021 | Balasamy et al. |
| 2002/0086049 A1 | 7/2002 | Bolton et al. |
| 2006/0002852 A1 | 1/2006 | Saltzman et al. |
| 2006/0222652 A1 | 10/2006 | Sebbel et al. |
| 2006/0251677 A1 | 11/2006 | Bachmann et al. |
| 2007/0219134 A1 | 9/2007 | Ruoslahti et al. |
| 2008/0014143 A1 | 1/2008 | Ruoslahti et al. |
| 2008/0035101 A1 | 2/2008 | Hausler et al. |
| 2008/0145441 A1 | 6/2008 | Penades et al. |
| 2009/0028910 A1 | 1/2009 | Desimone et al. |
| 2009/0036349 A1 | 2/2009 | Ruoslahti et al. |
| 2009/0226525 A1 | 9/2009 | De Los Rios et al. |
| 2019/0076373 A1 | 3/2019 | Bencherif et al. |
| 2020/0121810 A1 | 4/2020 | Li et al. |

FOREIGN PATENT DOCUMENTS

| | | | |
|---|---|---|---|
| WO | 2009106999 A2 | 9/2009 | |
| WO | 2010047839 A1 | 4/2010 | |
| WO | WO-2020186268 A1 * | 9/2020 | ........... A61B 5/0515 |
| WO | 2021005337 A1 | 1/2021 | |
| WO | 2021108674 A1 | 6/2021 | |

OTHER PUBLICATIONS

Zhang et al. Image-Guided High-Intensity Focused Ultrasound, A Novel Application for Interventional Nuclear Medicine?. J Nucl Med. 2021;62(9):1181-1188. (Year: 2021).*

Zhu et al. Vinblastine-Loaded Nanoparticles with Enhanced Tumor-Targeting Efficiency and Decreasing Toxicity: Developed by One-Step Molecular Imprinting Process. Molecular Pharmaceutics 2019 16 (6), 2675-2689. (Year: 2019).*

Nelson et al. J. Pharm. Sci. 2006, 95, 1527. (Year: 2006).*

Awad et al. Ultrasound-Responsive Nanocarriers in Cancer Treatment: A Review. ACS Pharmacol Transl Sci. 2021;4(2):589-612. (Year: 2021).*

Moad et al. Azo and Peroxy Initiators. Comprehensive Polymer Science and Supplements 8 (1996): 97-121. (Year: 1996).*

Bakaic et al, "Injectable Hydrogels Based on Poly(Ethylene Glycol) and Derivatives as Functional Biomaterials", RSC Advances, vol. 5, pp. 35469-35486, Apr. 13, 2015.

Hamzah et al, "Specific penetration and accumulation of a homing peptide within atherosclerotic plaques of apolipoprotein E-deficient mice", PNAS, vol. 108, No. 17, pp. 7154-7159, Apr. 26, 2011.

International Search Report and Written Opinion of the International Searching Authority issued in International Appl. No. PCT/US2022/078098, 9 pages, dated Dec. 30, 2022.

Joyce et al, "Stage-specific vascular markers revealed by phage display in a mouse model of pancreatic islet tumorigenesis", Cancer Cell, vol. 4, pp. 393-403, Nov. 2003.

Kim et al, "Abstract 1318: Mechanochemical dynamic therapy for focal cancer treatment", Cancer Res, vol. 81, 13 Supplement, pp. 1318, Apr. 10, 2021.

Kim et al, "Ultrasound controlled mechanophore activation in hydrogels for cancer therapy", PNAS, vol. 119, No. 4, 7 pages, Dec. 9, 2021.

Laakkonen et al, "A tumor-homing peptide with a targeting specificity related to lymphatic vessels", Nature Medicine, vol. 8, No. 7, 751-755, Jul. 2002.

Laakkonen et al, "Antitumor activity of a homing peptide that targets tumor lymphatics and tumor cells", PNAS, vol. 101, No. 25, pp. 9381-9386, Jun. 22, 2004.

Look et al, "Nanogel-based delivery of mycophenolic acid ameliorates systemic lupus erythematosus in mice", The Journal of Clinical Investigation, 9 pages, Mar. 1, 2013.

Moghimi et al, "Long-Circulating and Target-Specific Nanoparticles: Theory to Practice", Pharmacological Reviews, vol. 53, No. 2, pp. 283-318, (2001).

Paolicelli et al, "Surface-modified PLGA-based nanoparticles that can efficiently associate and deliver virus-like particles", Nanomedicine, vol. 5, No. 6, pp. 843-853, (2010).

Smith et al, "Mechanochemical dynamic therapy for focal cancer treatment" AACR Poster, (2021).

Sugahara et al, "Tissue-penetrating delivery of compounds and nanoparticles into tumors", Cancer Cell, vol. 16, No. 6, pp. 510-520, Dec. 2009.

Tong et al, "A Facile Mechanophore Functionalization of Amphipilic Block Copolymer towards Remote Ultrasound and Redox Dual Stimulus Responsiveness", Chemical Communications, No. 27, 10 pages, (2014).

Van Rooijen et al, "Liposome mediated depletion of macrophages: mechanism of action, preparation of liposomes and applications", Journal of Immunological Methods, vol. 174, pp. 83-93, (1994).

* cited by examiner

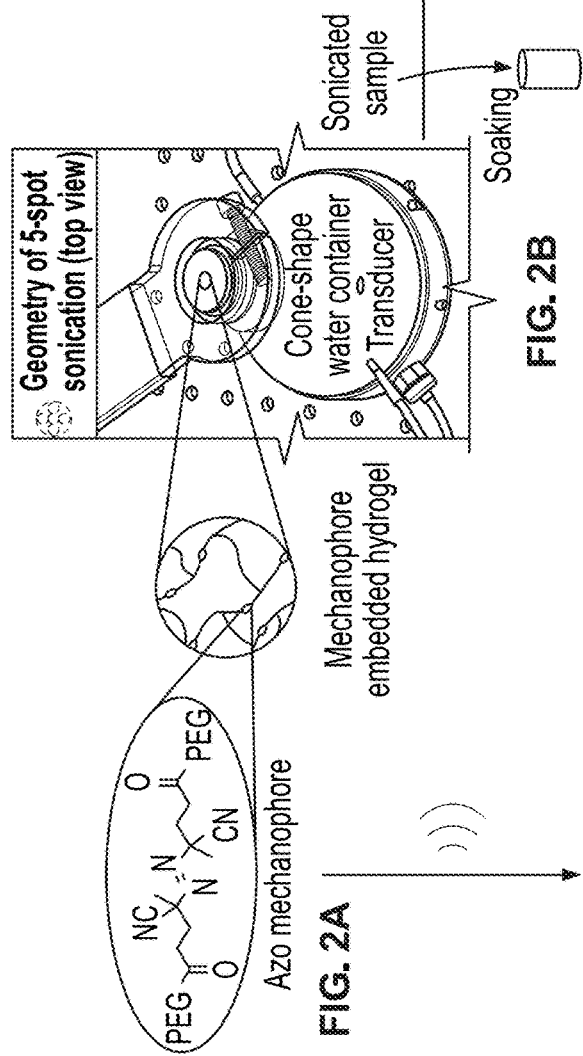
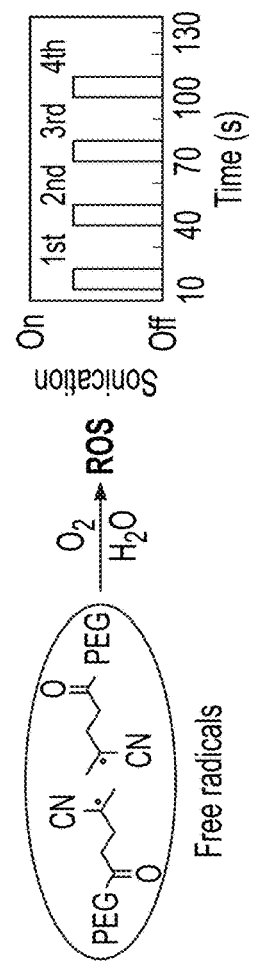
FIG. 2A  FIG. 2B  FIG. 2C  FIG. 2D

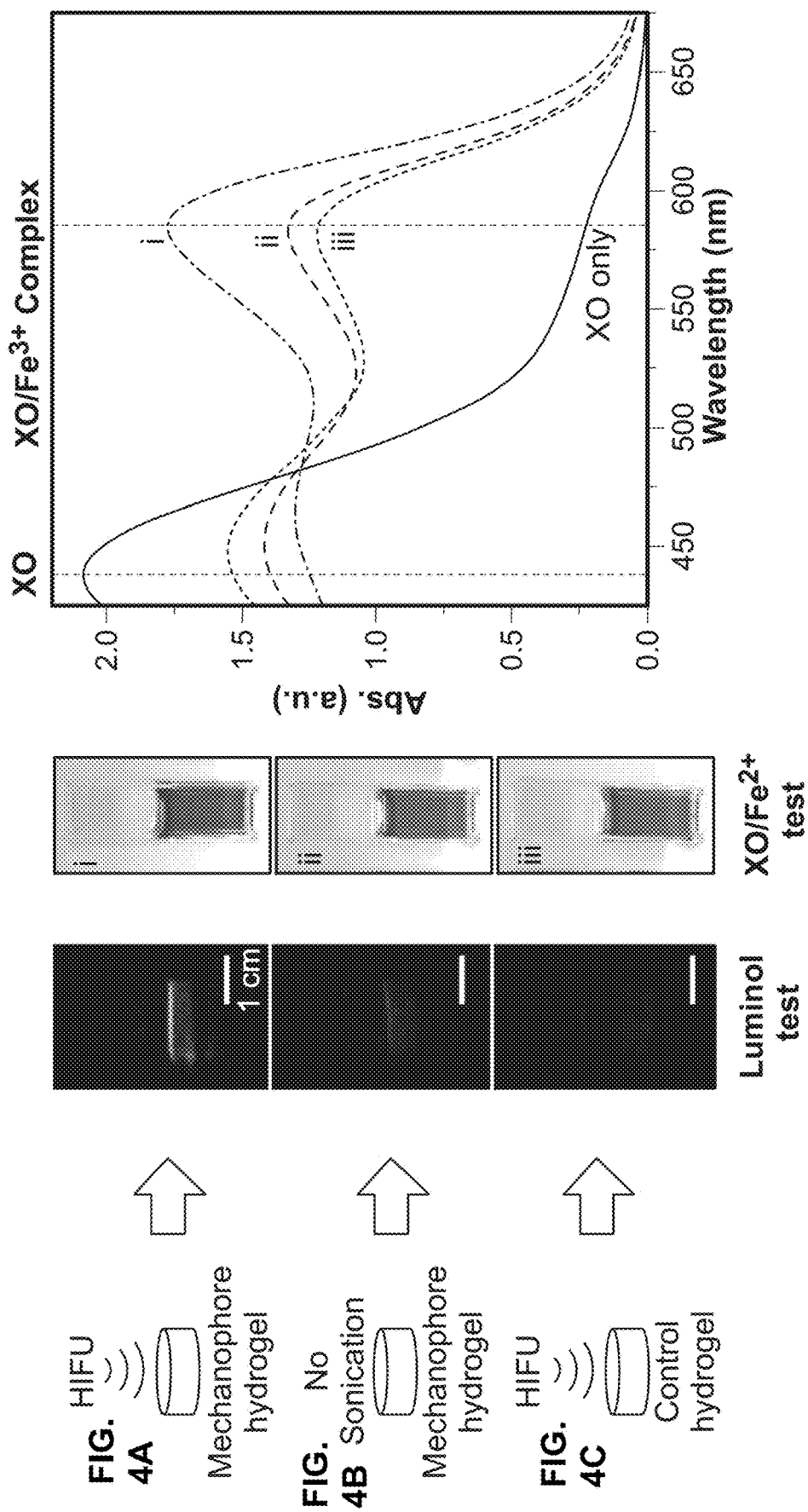

Experimental setup

MECHANOCHEMICAL DYNAMIC FOR FOCAL CANCER TREATMENT

PRIORITY

This application claims the benefit of U.S. Ser. No. 63/256,239 filed on Oct. 15, 2021, which is incorporated by reference herein in its entirety.

STATEMENT REGARDING FEDERALLY SPONSORED RESEARCH OR DEVELOPMENT

This invention was made with government support under R01CA184091-04 awarded by the National Institutes of Health. The United States Government has certain rights in the invention.

BACKGROUND

Mechanophores are molecular motifs that respond to mechanical perturbance with targeted chemical reactions toward desirable changes in material properties. A large variety of mechanophores have been investigated, with applications focusing on functional materials such as strain/stress sensors, nanolithography, and self-healing polymers, among others. The responses of engineered mechanophores, such as light emittance, change in fluorescence, and generation of free radicals (FRs), however, have not been explored for bioimaging, biomedical, and therapy applications.

SUMMARY

Provided herein are compositions comprising one or more azo-mechanophores, peroxide-mechanophores, or disulfide-mechanophores covalently linked to a hydrogel matrix or biodegradable elastomer matrix wherein the one or more azo-mechanophores, peroxide-mechanophores, or disulfide-mechanophores are present in the hydrogel matrix or biodegradable elastomer matrix at about 3.0 wt % to about 15 wt %. The composition can have a diameter or width of about 0.5 µM to about 10 mm. The hydrogel matrix can comprise polydimethylsiloxane (PDMS) or polyethylene glycol (PEG).

An aspect provides a method of generating reactive oxygen species comprising contacting the compositions described herein with high intensity focused ultrasound (HIFU).

Another aspect provides a method of killing cells, tissue, or tumors comprising delivering the compositions described herein to the cells, tissue, or tumors and activating the azo-mechanophores, peroxide-mechanophores, or disulfide-mechanophores with HIFU. The cells, tissue, or tumors can be cancerous and can be present in a mammal. The methods can further comprise delivering one or more additional cancer therapies to the mammal. The cells, tissue, or tumors can be present in vitro. The azo-mechanophores, peroxide-mechanophores, or disulfide-mechanophores can mechanically generate free radicals when subjected to the HIFU, which are converted to reactive oxygen species. The reactive oxygen species can kill the cells, tissue, or tumors via oxidative cytotoxicity, apoptosis, or both. The HIFU can penetrate into the cells, tissue, or tumors to a depth of more than 1 cm. The HIFU can delivers continuous wave ultrasound at about 500 to about 600 kHz. The HIFU can deliver continuous wave ultrasound in a pulse, wherein the pulse can be delivered once, twice, or by repeated pulsing.

Even another aspect provides a composition comprising one or more azo-mechanophores, peroxide-mechanophores, or disulfide-mechanophores and a nanocarrier wherein the azo-mechanophores, peroxide-mechanophores, or disulfide-mechanophores comprise about 3.0 wt % to about 15 wt % of the composition. The one or more azo-mechanophores, peroxide-mechanophores, or disulfide-mechanophores can be loaded into the nanocarrier or can be covalently, or non-covalently linked to the nanocarrier. The nanocarrier can comprise lipids, polymers, iron oxide, liposomes, micelles, lipoproteins, lipid-coated bubbles, block copolymer micelles, polymersomes, niosomes, iron oxide particles, gold particles, silica particles, dendrimers, quantum dots, polymer nanogels, polymer-functionalized nanoparticles, polymer vesicles, or combinations thereof. The compositions can further comprise one or more tumor-homing compounds.

Another aspect provides a method of killing cells, tissue, or tumors comprising delivering the nanocarrier compositions described herein to the cells, tissue, or tumors and activating the azo-mechanophores, peroxide-mechanophores, or disulfide-mechanophores with HIFU. The cells, tissue, or tumors can be cancerous and can be present in a mammal. The method can further comprise delivering one or more additional cancer therapies to the mammal. The cells, tissue, or tumors can be present in vitro. The azo-mechanophores, peroxide-mechanophores, or disulfide-mechanophores can mechanically generate free radicals when subjected to the HIFU, which are converted to reactive oxygen species. The reactive oxygen species can kill the cells, tissue, or tumors via oxidative cytotoxicity, apoptosis, or both. The HIFU can penetrate into the cells, tissue, or tumors to a depth of more than 1 cm. The HIFU can deliver continuous wave ultrasound at about 500 to about 600 kHz. The HIFU can deliver continuous wave ultrasound in a pulse, wherein the pulse can be delivered once, twice, or by repeated pulsing.

BRIEF DESCRIPTION OF THE DRAWINGS

Various objectives, features, and advantages of the disclosed subject matter can be more fully appreciated with reference to the following detailed description of the disclosed subject matter when considered in connection with the following drawings, in which like reference numerals identify like elements.

FIGS. 2A-2D show HIFU setup and in vivo design. (FIG. 2A) The structure of azo-based mechanophore hydrogel for the generation of FRs and ROS under sonication. (FIG. 2B) The sonication setup. (FIG. 2C) The sonication cycles (4 repetitions for each spot). (FIG. 2D) The detection of ROS and in vitro treatment.

(FIG. 3A) Thermal decomposition rate of the azo-mechanophore, calculated from the kinetics data of the azo-PEG macroinitiator. (FIG. 3B) Cytotoxicity evaluation of mechanophore and control hydrogels without sonication for melanoma cells (n≥4) under physiological conditions (37° C., pH 7.4, 5% CO2/95% $O_2$).

FIGS. 4A-4C show luminol chemiluminescence and XO/$Fe^{2+}$ colorimetric tests for (FIG. 4A) sonicated mechanophore hydrogels, (FIG. 4B) mechanophore hydrogels without sonication and (FIG. 4C) sonicated control hydrogels. UV-Vis colorimetric analysis was taken after immersing samples in XO/$Fe^{2+}$ for 30 minutes and compared with XO only control (no hydrogel).

(FIG. 8A) HIFU setup and designed cone-shape water container with HFU transducer; and (FIG. 8B) Hydrogel-transducer assembly.

(FIG. 9A) IR image of azo-mechanophore hydrogel at the peak temperature of each sonication cycle. (FIG. 9B) Temperature profile measured by IR camera at the focal spot. (FIG. 9C) Temperature profile measured by a thermocouple inserted into the center of hydrogel at the focal spot.

(FIG. 11A) Ultrasonic setup for the estimation of acoustic properties of PEG hydrogels with and without mechanophores. (FIG. 11B) Example of the measured time domain signal obtained from the TOF method (center frequency of 10 MHz). (FIG. 11C) Example of the measured attenuation coefficient signal (center frequency of 10 MHz).

(FIG. 12A) Experimental setup of in vitro MDT and control cells with example images of Calcein-AM viability stain, and (FIG. 12B) Example of counting Calcein-AM-positive viable cells using the ImageJ software provided by NIH.

Figure 1:
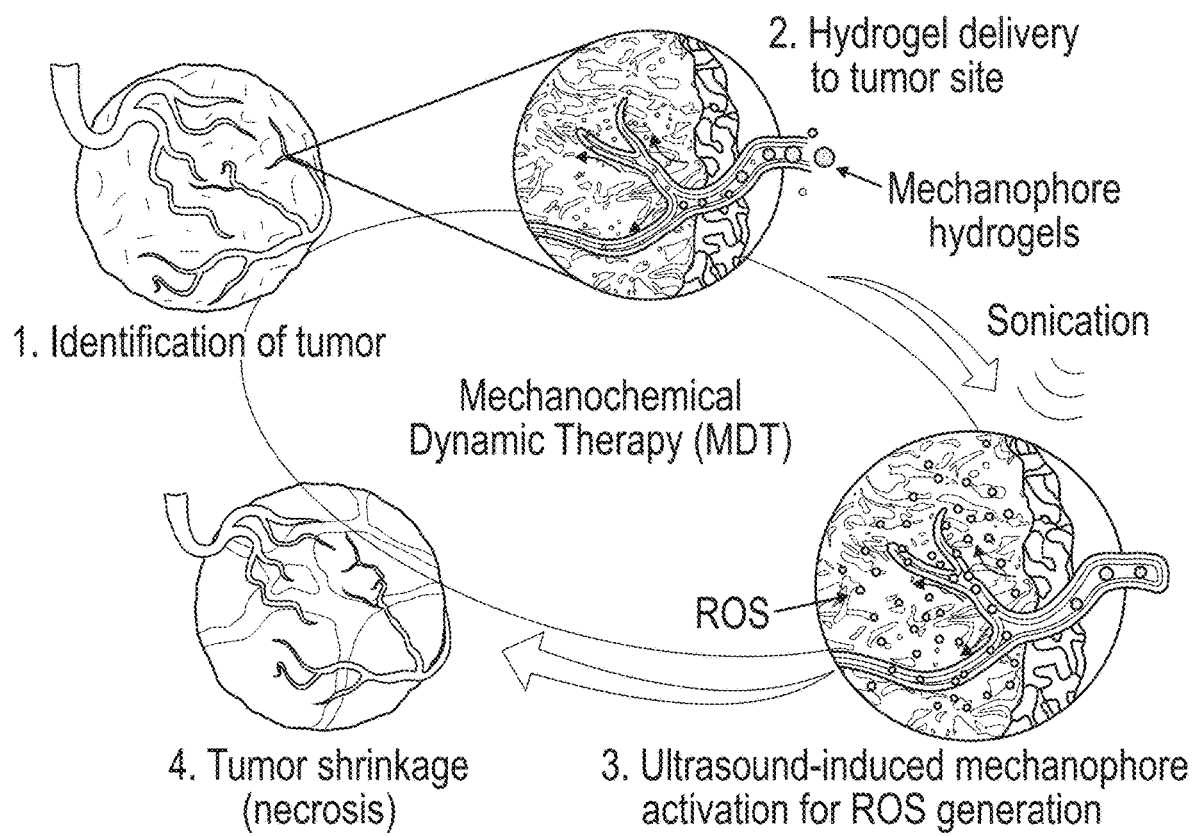
FIG. 1 shows the concept of MDT: Focused ultrasound controls reactive oxygen species (ROS) generation from mechanochemical reactions for non-invasive cancer therapy.

The drawings are not necessarily to scale, or inclusive of all elements of a system, emphasis instead generally being placed upon illustrating the concepts, structures, and techniques sought to be protected herein.

DETAILED DESCRIPTION

The compositions and methods are more particularly described below and the Examples set forth herein are intended as illustrative only, as numerous modifications and variations therein will be apparent to those skilled in the art.

Overview

Compositions and methods for mechanochemical dynamic therapy (MDT) that utilizes remote, ultrasound-triggered mechanophore activation to enable anti-cancer activities are provided herein.

Mechanophores

Provided herein is a gelled composition that can comprise one or more azo-mechanophores, peroxide-mechanophores, or disulfide-mechanophores covalently linked to a hydrogel or elastomer wherein the azo-mechanophores, peroxide-mechanophores, or disulfide-mechanophores are present within the hydrogel.

A mechanophore is a mechanically-sensitive compound that responds to mechanical force with a chemical change.

A mechanophore can be present in a polymer backbone only, in the crosslinkages only, or in both in the polymer backbone and the crosslinkages. The polymer can be a linear polymer or a crosslinked polymer (e.g., a hydrogel). In some embodiments, a mechanophore can comprise moieties such as an azo group, triazole group, peroxo group, disulfide group, cyclobutyl group, or a combination thereof. In some embodiments, a mechanophore can comprise moieties such as an azo group, peroxo group, and disulfide group, or a combination thereof.

In some embodiments, a mechanophore is an azo-mechanophore. In some embodiments, an azo-mechanophore is an aliphatic azo-mechanophore. In some embodiments, an azo-mechanophore is an aliphatic azo-mechanophore that is stable at body temperature (e.g., about 37°) or at about 30, 31, 32, 33, 34, 35, 36, 37, 38, 39, 40° C. or more. In some embodiments, an azo-mechanophore includes azonitrile compounds, such as azobisisobutylonitrile, 4,4'-azobis(4-cyanovaleric acid), 2,2'-azobis(4-methoxy-2,4-dimethyl-valeronitrile), 1,1'-azobis(cyclohexane-1-carbonitrile), 1-(1-cyano methylethyl)azoformamide and 2-phenylazo-4-methoxy-2,4-dimethylvaleronitrile; azoamidine compounds, such as 2,2'-azobis(2-methylpropionamidine) dihydrochloride; cyclic azoamidine compounds, such as 2,2'-azobis-2-(2-imidazolin-2-yl)propane; azoamide compounds, such as 2,2'-azobis(2-methyl-n-1,1-bis(hydroxymethyl)-2-hydroxyethyl propyonamide) and 2,2'-azobis(2-methyl-n-1,1 bis(hydroxymethyl)ethyl) propionamide; alkylazo compounds, such as 2,2'-azobis(2,4,4-trimethylpentane). In some embodiments, an azo-mechanophore can be used alone or in combination of two or more.

In some embodiments, a mechanophore is a peroxide-mechanophore. In some embodiments, a peroxide-mechanophore includes ketone peroxides, such as methyl ethyl ketone peroxide, cyclohexanone peroxide, 3,3,5-trimethylcyclohexanone peroxide, methylcyclohexanone peroxide, methylacetoacetate peroxide and acetylacetone peroxide; peroxyketals, such as 1,1-bis(tert-butylperoxy)-3,3,5-trimethylcyclohexane, 1,1-bis(tert-butylperoxy)cyclohexane, 2,2-bis(tert-butylperoxy)octane, n-butyl-4,4-bis(tert-butylperoxy)valerate and 2,2-bis(tert-butylperoxy)butane; hydroperoxides, such as tert-butyl hydroperoxide, cumene hydroperoxide, diisopropylbenzene hydroperoxide, paramethane hydroperoxide, 2,5-dimethylhexane-2,5-dihydroperoxide and 1,1,3,3-tetramethylbuthyl hydroperoxide; dialkyl peroxides, such as di-tert-butyl peroxide, tert-butylcumyl peroxide, dicumyl peroxide, alpha,alpha'-bis(tert-butylperoxy-meta-isopropyl)benzene, 2,5-dimethyl-2,5-di(tert-butylperoxy)hexane and 2,5-dimethyl-2,5-di(tert-butylperoxy)hexyne-3; diacyl peroxides, such as acetyl peroxide, isobutyl peroxide, octanoyl peroxide, decanoyl peroxide, lauryonyl peroxide, 3,3,5-trimethylhexanoyl peroxide, succinic acid peroxide, benzoyl peroxide, 2,4-dichlorobenzoyl peroxide and m-toluoyl peroxide; peroxydicarbonates, such as diisopropyl peroxydicarbonate, di-2-ethylhexyl peroxydicarbonate, di-n-propyl peroxydicarbonate, bis(4-tert-butylcyclohexyl) peroxydicarbonate, di-2-ethoxyethyl peroxydicarbonate, dimethoxyisopropyl peroxydicarbonate, di(3-methyl-3-methoxybutyl) peroxydicarbonate and diallyl peroxydicarbonate; peroxy esters, such as tert-butyl peroxy acetate, tert-butyl peroxy isobutylate, tert-butyl peroxy pivalate, tert-butyl peroxy neodecanoate, cumyl peroxy neodecanoate, tert-butyl peroxy-2-ethylhexanoate, tert-butyl peroxy-3,3,5-trimethyl hexanoate, tert-butyl peroxy laurate, tert-butyl peroxy benzoate, di-tert-butyl peroxy isophthalate, 2,5-dimethyl-2,5-di(benzoyl peroxy)hexane, tert-butyl peroxymaleic acid, tert-butyl peroxy isopropyl carbonate, cumyl peroxy octoate, tert-hexyl peroxy neodecanoate, tert-hexyl peroxy pivalate, tert-butyl peroxy neohexanoate, tert-hexyl peroxy neohexanoate and cumyl peroxy neohexanoate; and other organic peroxides: such as acetylcyclohexylsulfonyl peroxide and tert-butyl peroxyallyl carbonate. A peroxide-mechanophore can be used alone or in combination of two or more.

In some embodiments, a mechanophore can be a disulfide mechanophore. In some embodiments, a disulfide mechanophore can include: tetraalkylthiuram disulfides, such as tetramethylthiuram disulfide and the like; and diaryl disulfides such as dibenzoyl disulfide and the like. A disulfide mechanophore can be used alone or in a combination of two or more. In some embodiments, a gelled composition as described herein can comprise one or more azo-mechanophores, peroxide-mechanophores, or disulfide-mechanophores. In some embodiments, a nanocarrier composition as described herein can comprise one or more azo-mechanophores, peroxide-mechanophores, or disulfide-mechanophores.

In an aspect, a mechanophore is not a boron dye, or is not a difluoroboron dibenzoylmethane, or is not a difluoroboron dibenzoylmethane derivative.

Gel Matrices and Elastomer Matrices

A gelled composition provided herein can be a hydrogel matrix or elastomer matrix with one or more azo-mechanophores, peroxide-mechanophores, or disulfide-mechanophores linked to the hydrogel matrix or elastomer matrix.

Gels are substantially dilute cross-linked systems that exhibit no flow when in the steady-state. A gel is a wet solid-like material in which a solid network of interconnected nanostructures spans the volume of a liquid medium. The continuous phase is a solid network and the dispersed phase is a liquid. Gels tend to be mostly liquid in composition and typically exhibit the density of a liquid as result but have cohesiveness like a solid. Gel matrices and elastomer matrices can be comprised any type of suitable gel, such as hydrogels or silicone gels. In some embodiments, the gel or elastomer matrices are biodegradable. Gel matrices include, for example, arabinogalactan gel, arabinoxylan gel, galactan gel, galactomannan gel, lichenan gel, xylan gel, cellulose derivatives such as hydroxymethylpropyl cellulose, combined with a gel forming agent such as arabinogalactan, arabinoxylan, galactan, galactomannan, licenan, xylan, hydroxymethyl cellulose, protein gels, gelatin gels, whey protein gel, soy protein gel, casein gel, gels comprised of arabinogalactan; arabinoxylan; galactan; galactomannan; lichenan; xylan; casein; hyaluronic acid; chitosan; gum Arabic; carboxyvinyl polymer; sodium polyacrylate; carboxymethyl cellulose; sodium carboxymethyl cellulose; pullulan; polyvinylpyrrolidone; karaya gum; pectin; xanthane gum; tragacanth; alginic acid; polyoxymethylene; polyimide; polyether; chitin; poly-glycolic acid; poly-lactic acid; co-polymer of poly-glycolic and poly-lactic acid; co-polymer of poly-lactic acid and polyethylene oxide; polyamide; polyanhydride; polycaprolactone; maleic anhydride copolymer; poly-hydroxybutyrate co-polymer; poly(1,3-bis(p-carbophenoxy)propane anhydride); polymer formed by co-polymerization with sebacic acid or with poly-terephthalic acid; poly(glycolide-co-trimethylene carbonate); polyethylene glycol; polydioxanone; polypropylene fumarate; poly (ethyl glutamate-co-glutamic acid); poly(tert-butyloxy carbonylmethyl glutamate); poly-caprolactone; poly (caprolactone-co-butylacrylate); poly-hydroxybutyrate and copolymers thereof; poly(phosphazene); poly(D,L-lactide-co-caprolactone); poly(glycolide-co-caprolactone); poly (phosphate ester); poly(amino acid); poly(hydroxybutyrate); polydepsidpeptide; maleic anhydride copolymer; polyphosphazene; polyiminocarbonate; poly[(7.5% dimethyl-trimethylene carbonate)-co-(2.5% trimethlyene carbonate)]; polyethylene oxide; hydroxypropylmethylcellulose, poly (ethylene-co-vinyl acetate); isobutylene-based copolymer of isobutylene and at least one other repeating unit such as butyl acrylate: butyl methacrylate; substituted styrene such as amino styrene, hydroxy styrene, carboxy styrene, sulfonated styrene; homopolymer of polyvinyl alcohol; co-polymer of polyvinyl alcohol and at least one other repeating unit such as a vinyl cyclohexyl ether; hydroxymethyl methacrylate; hydroxyl- or amino-terminated polyethylene glycol; acrylate-based copolymer such as methacrylic acid, methacrylamide, hydroxymethyl methacrylate; ethylene vinyl alcohol copolymer; silicone based copolymer of aryl or alkyl siloxane and at least one repeating unit; polyurethane; heparan sulfate; RGD peptide; polyethylene oxide; chrondroitin sulfate; YIGSR peptides; keratan sulfate; VEGF biomimetic peptide; perlecan (heparan sulfate proteoglycan 2); modified heparin; fibrin fragments; and combinations thereof. Any suitable gel or elastomer matrices can be used. Any biocompatible polymeric material can be used.

Hydrogel matrices are generally characterized as having a crosslinked polymer matrix component that expands when contacted with a sufficiently compatible fluid such as water. Hydrogel matrices generally exhibit biocompatibility and biodegradable qualities.

Elastomer matrices are made up of polymers with viscoelasticity (i.e., both viscosity and elasticity). Elastomeric materials can be used to make an elastomer matrix including, for example, thermoplastic elastomers, polyolefin elastormers, polydiene elastomers, poly(vinyl chloride), natural rubber, heparinized polymers, hydrogels, polypeptide elastomers, and combinations thereof. In some embodiments, any suitable elastomer can be used.

In some embodiments a gel or elastomer matrix is biocompatible.

In some embodiments, biodegradable or biocompatible elastomers can be used, such as hydrogels, elastin-like-peptides (ELP), or polyhydroxyalkanoates (PHAs). An ELP is a synthetic protein containing structural peptide units, which can be repeating units, structurally related to, or derived from, sequences of the elastin protein. ELPs comprise repeat units of a Val-Pro-Gly-X-Gly (SEQ ID NO:13) motif derived from the hydrophobic domain of tropoelastin, where X represents any amino acid. In some embodiments the X is not proline. In some embodiments, an ELP can comprise one or more of the motifs including, but not limited to, (A) tetrapeptide Val-Pro-Gly-Gly, or VPGG (SEQ ID NO:1); (B) tetrapeptide Ile-Pro-Gly-Gly, or IPGG (SEQ ID NO:2); (C) pentapeptide Val-Pro-Gly-X-Gly (SEQ ID NO:3) or VPGXG, where X is any amino acid residue, natural or non-natural, and X is optionally a repeat of the polymer; (D) pentapeptide Ala-Val-Gly-Val-Pro, or AVGVP (SEQ ID NO:4); (E) pentapeptide Ile-Pro-Gly-X-Gly, or IPGXG (SEQ ID NO:5), where X is any amino acid residue, natural or non-natural; (F) pentapeptide Ile-Pro-Gly-Val-Gly, or IPGVG (SEQ ID NO:6); (G) pentapeptide Leu-Pro-Gly-X-Gly, or LPGXG (SEQ ID NO:7), where X is any amino acid residue, natural or non-natural; (H) pentapeptide Leu-Pro-Gly-Val-Gly, or LPGVG (SEQ ID NO:8); (I) hexapeptide Val-Ala-Pro-Gly-Val-Gly, or VAPGVG (SEQ ID NO:9); (J) octapeptide Gly-Val-Gly-Val-Pro-Gly-Val-Gly, or GVGVPGVG (SEQ ID NO:10); (K) nonapeptide Val-Pro-Gly-Phe-Gly-Val-Gly-Ala-Gly, or VPGFVGGAG (SEQ ID NO:11); or (L) nonapeptide Val-Pro-Gly-Val-Gly-Val-Pro-Gly-Gly, or VPGVGVPGG (SEQ ID NO:12). An ELP can contain motifs having a 5 to 15-unit repeat (e.g., about 10-unit repeat) of the peptides described above, with the X amino acid varying among at least 2 or at least 3 of the repeated units.

PHAs comprise a group of natural biodegradable polyesters that are synthesized by microorganisms. PHAs include, but are not limited to, poly-beta-hydroxybutyrate (PHB), polyhydroxyvalerate (PHV), polyhydroxybutyrate-covalerate (PHB/V), and polyhydroxyhexanoate (PHH). Any suitable biodegradable elastomer matrix can be used.

The biodegradable components of the gel or elastomeric matrix can degrade by, for example, hydrolysis or by enzymatic activity. In one embodiment, the biodegradable components of the gel or elastomeric matrix can bio-degrade or can be broken down into innocuous, nontoxic or biocompatible products. The degradation product does not evoke unusual inflammatory response/toxic response and is metabolized by the body in a biocompatible fashion that is characterized by the absence of or extremely low: cytotoxicity, hemotoxicity, carcinogenicity, mutagenicity, or teratogenicity.

Hydrogels and elastomer matrices can be made up of natural materials or synthetic materials or combinations thereof. Suitable biodegradable natural gel or hydrogel matrices can be made up of, for example, collagen, gelatin, fibrin, chitosan, hyaluronic acid, chondroitin sulfate, alginate, or agar/agarose. Suitable biodegradable synthetic gel or hydrogel matrices can be made up of polyethylene (PE), polyethylene glycol (PEG), polyethylene oxide (PEO), polyvinyl acetate (PVA), poly(propylene fumarate) (PPF), oligo (poly(ethylene glycol) fumarate) (OPF), polypropylene (PP), poly(N-isopropylacrylamide) (PNIPA, PNIPAAm, NIPA, PNIPAA or PNIPAm), PEO-PPO-PEO, PLGA-PEG, PLGA, PEG-PLLA-PEG, PCL-PEG-PCL, PCLA-PEG-PCLA, PEG-PCL-PEG, poly(aldehyde guluronate), polyanhydrides, or combinations thereof.

Other hydrogel or elastomer matrices can be made up of, for example, polyethylene glycol diacrylate (PEGDA), poly (ethylene glycol)-dimethacrylate (PEGDMA) poly(oligoethylene glycol methacrylate, polyacrylamide, polylysine, polydimethylsiloxane (PDMS), poly(lactic) acid (PLA), poly-L-lactide (PLLA), polysulfone, polyvinylchloride (PVC), polytetrafluoroethylene (PTFE), polyetheretherketone (PEEK), poly(lactic-co-glycolic acid) (PLGA), poly (propylene fumarate) (PPF), Polycaprolactone (PCL), polyphenylene oxide (PPO), acrylated forms of polyethylene glycol, acrylated forms of polydimethylsiloxane, acrylated forms of polyacrylamide, or combinations thereof.

Hydrogel matrices are three-dimensional networks of hydrophilic polymer chains, in which retained water constitutes at least about 20% of the weight (for example about 20, 30, 40, 50, 60% or more). In some embodiments the retained water can be about 70, 60, 50, 40, 30, 25, 21% or less of the weight. In some embodiments a hydrogel matrix is biocompatible. A biocompatible hydrogel matrix performs its desired function, without eliciting significant undesirable local or systemic effects in the patient or recipient (e.g., cells, tissues, mammals), while generating the most appropriate beneficial cellular or tissue response.

In some embodiments, a hydrogel matrix can comprise polydimethylsiloxane (PDMS) or polyethylene glycol (PEG).

In some embodiments, a gel or elastomer matrix is a PEG matrix that is not thiol-ene based. See, e.g., Bakaic et al., RSC Advances, 5:35469 (2015).

In some embodiments, one or more azo-mechanophores, peroxide-mechanophores, or disulfide-mechanophores are covalently crosslinked or non-covalently bonded to the hydrogel or elastomer matrix providing a gelled composition comprising, for example, azo-mechanophores, peroxide-mechanophores, or disulfide-mechanophores covalently linked (by any suitable means) to a hydrogel or elastomer matrix. One or more azo-mechanophores, peroxide-mechanophores, or disulfide-mechanophores can be present in a hydrogel or elastomer matrix at about 0.5, 1.0, 2.0, 3.0, 4.0, 5.0, 6.0, 7.0, 8.0, 9.0, 10.0, 11.0, 12.0, 13.0, 14.0, 15.0, 16.0, 17.0, 18.0, 19.0, 20.0 wt % (percentage by weight) or more. One or more azo-mechanophores, peroxide-mechanophores, or disulfide-mechanophores can be present in a hydrogel or elastomer matrix at about 20.0, 19.0, 18.0, 17.0, 16.0, 15.0, 14.0, 13.0, 12.0, 11.0, 10.0, 9.0, 8.0, 7.0, 6.0, 5.0, 4.0, 3.0, 2.0, 1.0, 0.5 wt % or less.

A hydrogel or elastomer matrix can be any size or shape. For example, a gel elastomer matrix can be a cylinder, sphere, plane, circular sheet, other shaped sheet, slab, irregular, or cube shape. A hydrogel or elastomer matrix can have any dimension. In some embodiments a hydrogel or elastomer matrix is about 0.01, 0.05, 0.1, 0.5, 0.8, 1.0, 5, 10, 20, 30, 40, 50, 60, 70, 80, 90, 100 µM or more thick, or about 0.2 mm, 0.3 mm, 0.4 mm, 0.5 mm, 1 mm, 5 mm, 10 mm, 20 mm, 50 mm or more thick. In some embodiments, wherein the gel matrix is a cylinder, sphere or circular, the diameter of the gel matrix can be about 0.01, 0.05, 0.1, 0.5, 0.8, 1.0, 5, 10, 20, 30, 40, 50, 60, 70, 80, 90, 100 µM or more, or about 0.2 mm, 0.3 mm, 0.4 mm, 0.5 mm, 1 mm, 5 mm, 10 mm, 20 mm, 50 mm or more.

The amount of mechanophore coupled to a gel is based on the total dry recipe weight of materials in an entire gel (weight/weight). The amount of mechanophores in a gel can be about 1, 2, 3, 4, 5, 6, 7, 8, 9, 10, 11, 12, 13, 14, 15, 20, 25, 30, 40, 50 wt % or more.

In some embodiments, one or more azo-mechanophores, peroxide-mechanophores, or disulfide-mechanophores are not present in a solution or liquid (as an end product), but is non-covalently bonded, covalently linked or bonded, or covalently crosslinked to a gel or elastomer matrix. Crosslinking is the process of forming bonds (e.g., covalent or non-covalent bonds) or relatively short sequences of chemical bonds to join polymer chains together. Non-covalent bonds can be, for example, hydrogen bonds, Van der Waals interactions, hydrophobic bonds, and/or ionic bonds.

High-Intensity Focused Ultrasound

Also provided herein is a method of generating reactive oxygen species comprising contacting the gelled compositions disclosed herein (e.g., a hydrogel or elastomer matrix linked with one or more azo-mechanophores, peroxide-mechanophores, or disulfide-mechanophores) with high intensity focused ultrasound (HIFU). Also provided herein is a method of generating reactive oxygen species comprising contacting the nanocarrier compositions disclosed herein (e.g., one or more azo-mechanophores, peroxide-mechanophores, or disulfide-mechanophores loaded into, covalently or non-covalently linked to, for example, a micelle or quantum dots) with high intensity focused ultrasound (HIFU).

HIFU can be used as a stimulus for precision medicine due to its non-invasive nature and superior ability to penetrate biological tissue compared to other spatiotemporally-resolved stimuli such as light. By focusing an ultrasonic wave onto a target location, the high intensity of irradiation achieves mechanical deformation and cavitation in response to the acoustic pressure wave, as well as localized heating from energy dissipation. HIFU can also be referred to as magnetic resonance guided focused ultrasound surgery (MRgFUS) or Focused Ultrasound Surgery (FUS) when Magnetic Resonance Imaging is used for guiding the focused ultrasound energy deposition.

HIFU can also be, for example, image-guided HIFU. Image-guided high-intensity focused ultrasound is a therapeutic technology, permitting extracorporeal or endocavitary delivery of targeted thermal ablation while minimizing injury to any surrounding structures. In some embodiments, image-guided HIFU can facilitate spatiotemporally precise release of ROS at, for example a tumor site. Any suitable HIFU can be used.

HIFU (e.g., FUS Instruments, Canada) can be used to generate continuous wave ultrasound at a center frequency of about 400 kHz to about 1 MHz. In some embodiments, an HIFU transducer is used at a center frequency of about 400, 500, 600, 700, 800, 900, 1,000 kHz or more for about 5, 10, 20, 30, 60, 90, 120 seconds or more. The HIFU transducer can be at a focal distance of about 2,000, 1,000, 900, 800, 700, 600, 500, 400, 300, 200, 100, 90, 80, 70, 60, 50, 40, 30 mm or less to the gelled composition structure. The effective acoustic pressure level triggered by the HIFU can be about 2.1, 2.2, 2.3, 2.4, 2.5, 2.6, 2.7, 2.8, 2.9, 3.0, 3.1, 3.2, 3.3 MPa or more. The intensity (I) the HIFU can be about 35, 39.4, 40, 50, 75, 100, 150, 200, 250, 300, 325, 350, 370, 375, 376, 380, 390, 400 W·cm$^{-2}$ or more. The focal size of the ultrasound can be about half the wavelength of the ultrasound to about 1, 2, 3, 5, 10, 15, 20 cm or more. The beam width ($B_w$) of the transducer can be about 1 mm, 10 mm, 50 mm, 100 mm, 200 mm, 30 cm or more. In some embodiments, the beam width of the transducer is about 1.3 mm to about 3.1 mm.

In some embodiments, a barrier is present between the HIFU transducer and the gelled composition or target structure (e.g., cells, tissue, or tumor). A barrier can be, for example, bone, skin, blood, cells, tissue, plastic, glass, or other composition.

In some embodiments, a barrier is present between the HIFU transducer and the nanocarrier composition or target structure (e.g., cells, tissue, or tumor).

In some embodiments, HIFU can deliver continuous wave ultrasound at about 400, 450, 500, 550, 600, or 650 kHz (or any range between about 400 and 650 kHz (e.g., from about 500 to about 600 kHz or from about 450 to about 600 kHz)).

In some embodiments, HIFU can deliver continuous wave ultrasound for a pulse. In some embodiments, the HIFU can deliver continuous wave ultrasound in 1, 2, 3, 4, 5, 6, 7, 8, 9, 10, or more pulses. In some embodiments, the HIFU can repeat the pulse 1, 2, 3, 4, 5, 6, 7, 8, 9, 10, or more times (e.g., repeated pulses). In some embodiments, the HIFU can deliver continuous wave ultrasound in one or more pulses of different durations. In some embodiments the HIFU can deliver continuous wave ultrasound in a repeated pulse of a fixed duration.

Free Radicals and Reactive Oxygen Species

A free radical is an atom or molecule containing one or more unpaired electrons in valency shell or outer orbit and is capable of independent existence. The odd number of electron(s) of a free radical makes it unstable, short lived, and highly reactive. Because of their high reactivity, they can abstract electrons from other compounds to attain stability. Thus, the attacked molecule loses its electron and becomes a free radical itself, beginning a chain reaction cascade which finally damages the living cell. Both reactive oxygen species (ROS) and reactive nitrogen species (RNS) collectively constitute the free radicals and other non-radical reactive species.

Both the ROS and RNS can be classified into two groups of compounds namely; radicals and non-radicals. Radicals are the species that contain at least one unpaired electron in the shells around the atomic nucleus and are capable of independent existence. The oxygen molecule itself is a radical, and because of the presence of two unpaired electrons it is referred as biradical. Examples of the radicals can include, for example, Superoxide ($O_2^-\cdot$), Oxygen radical ($O_2\cdot$), Hydroxyl (OH·), Alkoxyradical (RO·), Peroxyl radical (ROO·), Nitric oxide (nitrogen monoxide) (NO) and nitrogen dioxide ($NO_2\cdot$). The high reactivity of these radicals is due to the presence of one unpaired electron which tends to donate it or to obtain another electron to attain stability. The non-radical species can include, for example, hydrogen peroxide ($H_2O_2$), hypochlorous acid (HOCl), hypobromous acid (HOBr), ozone ($O_3$), singlet oxygen ($^1O_2$), nitrous acid ($HNO_2$), nitrosyl cation ($NO^+$), nitroxyl anion ($NO^-$), dinitrogen trioxide ($N_2O_3$), dinitrogen tetraoxide ($N_2O_4$), nitronium (nitryl) cation ($NO_2^+$), organic peroxides (ROOH), aldehydes (HCOR) and peroxynitrite (ONOOH). These non-radical species are not free radicals but can lead to free radical reactions in living organisms.

In some embodiments, the azo-mechanophores, peroxide-mechanophores, or disulfide-mechanophores mechanically generate free radicals when subjected to the HIFU.

Free radicals can be ROS or RNS. ROS refers to unstable, reactive, partially reduced oxygen derivatives that are created as a by-product of normal metabolic processes or induced in radical chain reactions. ROS can be, for example, superoxide ($O_2^-\cdot$), oxygen radical ($O_2\cdot$), hydroxyl (OH·), alkoxyradical (RO·), or peroxyl radical including both alkylperoxyl and hydroperoxyl radicals (ROO· where R=H). RNS refers to unstable, reactive, partially reduced nitrogen derivatives that are created as a by-product of normal metabolic processes or induced in radical chain reactions. RNS can be, for example, Nitric oxide (nitrogen monoxide) (NO·) and nitrogen dioxide ($NO_2\cdot$). ROS and RNS can act as second messengers in cell signaling, and contribute to various biological processes in normal and cancer cells.

Cytotoxicity is defined as the toxicity caused due to the action of agents on living cells. Cytotoxic agents can be, for example, chemotherapeutic agents or any substance that kills cells, including cancer cells. These agents can stop cancer cells from dividing and growing and can cause tumors to shrink in size. Oxidative cytotoxicity describes free radical production that is toxic to cells. Apoptosis is a process of cell death characterized by DNA cleavage, nuclear condensation and fragmentation, and plasma membrane blebbing that leads to phagocytosis of the cell without inducing an inflammatory response.

Delivery

Compositions described herein can be delivered to cells, tumors, or a patient in need thereof via any suitable method. For example, the compositions can be brought in contact with the cells or tumors or a site within a patient (e.g., site of a tumor). In other embodiments, the compositions can be delivered via injection (e.g., systemic injection), infusion, or implantation. Compositions can be delivered, for example, intravenously, intrathecally, intracerebrally, intraventricularly, intranasally, intratracheally, intra-aurally, intra-ocularly, or peri-ocularly, orally, rectally, transmucosally, inhalationally, transdermally, parenterally, subcutaneously, intradermally, intramuscularly, intracisternally, intranervally, intrapleurally, topically, intralymphatically, intracisternally, or intranerve.

Nanocarriers

A mechanophore can be loaded (e.g., encapsulated) into or covalently or non-covalently linked to a nanocarrier for delivery. A nanocarrier possesses at least one dimension that is less than or equal to 5 microns in size. The maximal dimension of a nanocarrier is the largest dimension of a nanocarrier measured along any axis of a nanocarrier. The maximal dimension of a nanocarrier can be less than or equal to 5 microns.

A nanocarrier can be one or more lipid-based nanoparticles (i.e., lipid nanoparticles, which are nanoparticles where the majority of the material that makes up the structure are lipids), polymeric nanoparticles, metallic nanoparticles (i.e., gold particles or iron oxide particles), liposomes, micelles, lipoproteins, lipid-coated bubbles, block copolymer micelles, polymersomes, niosomes, polymer nanogels, polymer-functionalized nanoparticles, polymer vesicles, surfactant-based emulsions, dendrimers, buckyballs, nanowires, virus-like particles (i.e., particles that are primarily made up of viral structural proteins but that are not infectious or have low infectivity), peptide or protein-based particles (i.e., particles where the majority of the material that makes up their structure are peptides or proteins, such as albumin nanoparticles) and/or nanoparticles comprised of a combination of nanomaterials such as lipid-polymer nanoparticles.

A wide variety of nanocarriers can be used to construct a targeted delivery composition. The properties, e.g., size, of the nanocarrier can depend on the type and/or application of the nanocarrier and other factors. Nanocarriers can comprise any shape such as spheres, spheroids, flats, plate shapes, tubes, cubes, cuboids, ovals, oblong, ellipses, cylinders, cones, pyramids, toroidal, and the like. Nanocarriers can comprise one or more surfaces. Suitable nanocarriers can range in size from a maximum dimension (e.g., diameter) of about 1 nm to about 1000 nm, about 10 nm to about 200 nm, and about 50 nm to about 150 nm.

Examples of nanocarriers include biodegradable nanoparticles (see e.g., U.S. Pat. Nos. 5,543,158 and 10,583,199); polymeric nanoparticles (see e.g., US Pat. Publ. 2006/0002852 and U.S. Pat. No. 9,687,553) lithographically constructed nanoparticles (see e.g., of US Pat. Publ. 2009/0028910; WO 2009/051837); carbohydrate based nanoparticles (see e.g., US Pat. Publ. 2008/0145441) protein nanoparticles (see e.g., US Pat. Publ. 2009/0226525), virus-like particles (see e.g., US Pat. Publ. 2006/0222652) nucleic acid attached virus-like particles (see e.g., US Pat. Publ. 2006/0251677); virus-like particles (see e.g. WO2010047839A1, WO2009106999A2), nanoprecipitated nanoparticles (see e.g., Paolicelli et al., "Surface-modified PLGA-based Nanoparticles that can Efficiently Associate and Deliver Virus-like Particles" Nanomedicine. 5(6):843-853 (2010)); apoptotic cells, apoptotic bodies or the synthetic or semisynthetic mimics (see e.g., U.S. Pat. Publ. 2002/0086049); nanogels (see e.g., Look et al., Nanogel-based delivery of mycophenolic acid ameliorates systemic lupus erythematosus in mice" J. Clinical Investigation 123 (4):1741-1749(2013)); micelles; gadolinium co-loaded liposomes, lipid-polymer hybrid nanoparticles, polymer nanocore shells, nanostructured lipid carriers (NLC); silica coated gold nanoparticles, zinc oxide quantum dots, polymers containing hydroxyapatite shell and a magnetic core of iron oxide nanoparticles, chitosan modified single walled carbon nanotubes, nanocomposites based on graphene oxide, porous magnetic nanoclusters with iodinated oil, silica nanoparticles (see e.g., U.S. Pat. Nos. 10,343,903, 10,143,660), dextran, gadolinium-embedded iron oxide, nanofibers, alginate/mechanophore modified complex nanoparticles, superparamagnetic iron oxide nanoshells, polyethylene glycol modified phospholipid micelles, dendrimire, polymeric micelles, folate-conjugated PEGylated PLGA nanoparticles, hierarchical siliceous mesosilicalite nanocarrier (see e.g., U.S. Pat. Nos. 11,096,911, 11,103,594, and 10,525,023), segregated telodendrimers (see e.g., U.S. Pat. Nos. 10,967,003 and 10,947,350) sequentially decomposable polypeptide-based nanocarriers (see e.g., U.S. Pat. No. 10,905,653), and dendritic polypeptide-based nanocarriers (see e.g., U.S. Pat. No. 9,943,606).

A population of nanocarriers can be relatively uniform in terms of size or shape. For example, at least 80%, at least 90%, or at least 95% of nanocarriers based on the total number of nanocarriers, can have a minimum dimension or maximum dimension that falls within 5%, 10%, or 20% of the average diameter or average dimension of the nanocarriers.

Nanocarriers can be solid or hollow and can comprise one or more same or different layers. In some embodiments, each layer can have a unique composition and unique properties relative to the other layer(s). For example, nanocarriers can have a core/shell structure, wherein the core is one layer (e.g., a polymeric core) and the shell is a second layer (e.g., a lipid bilayer or monolayer).

In some embodiments, a nanocarrier can comprise one or more lipids. A nanocarrier can comprise a liposome and/or comprise a lipid bilayer or lipid monolayer. A nanocarrier can comprise a micelle. In some embodiments, a nanocarrier can comprise a core comprising a polymeric matrix surrounded by a lipid layer (e.g., lipid bilayer, lipid monolayer, etc.). In some embodiments, a nanocarrier can comprise a non-polymeric core (e.g., metal particle, quantum dot, ceramic particle, bone particle, viral particle, proteins, nucleic acids, carbohydrates, etc.) surrounded by a lipid layer (e.g., lipid bilayer, lipid monolayer, etc.).

In some embodiments, nanocarriers can comprise one or more amphiphilic entities, which can provide increased stability, improved uniformity, or increased viscosity. An amphiphilic entity can be associated with, for example, an interior surface of a lipid membrane (e.g., lipid bilayer, lipid monolayer, etc.) of a nanocarrier. Examples of amphiphilic entities include phosphoglycerides; phosphatidylcholines; dipalmitoyl phosphatidylcholine (DPPC); dioleylphosphatidyl ethanolamine (DOPE); dioleyloxypropyltriethylammonium (DOTMA); dioleoylphosphatidylcholine; cholesterol; cholesterol ester; diacylglycerol; diacylglycerolsuccinate; diphosphatidyl glycerol (DPPG); hexanedecanol; fatty alcohols such as polyethylene glycol (PEG); polyoxyethylene-9-lauryl ether; surface active fatty acids, such as palmitic acid or oleic acid; fatty acids; fatty acid monoglycerides; fatty acid diglycerides; fatty acid amides; sorbitan trioleate (Span®85) glycocholate; sorbitan monolaurate (Span®20); polysorbate (Tween®), polyoxyethylene monostearate; surfactin; a poloxomer; a sorbitan fatty acid ester such as sorbitan trioleate; lecithin; lysolecithin; phosphatidylserine; phosphatidylinositol; sphingomyelin; phosphatidylethanolamine (cephalin); cardiolipin; phosphatidic acid; cerebrosides; dicetylphosphate; dipalmitoylphosphatidylglycerol; stearylamine; dodecylamine; hexadecyl-amine; acetyl palmitate; glycerol ricinoleate; hexadecyl sterate; isopropyl myristate; tyloxapol; poly (ethylene glycol) 5000 phosphatidylethanolamine; poly (ethylene glycol) 400-monostearate; phospholipids; synthetic and/or natural detergents having high surfactant properties; deoxycholates; cyclodextrins; chaotropic salts; ion pairing agents; and combinations thereof.

A nanocarrier can comprise one or more carbohydrates. A carbohydrate can comprise a monosaccharide or disaccharide, for example, glucose, fructose, galactose, ribose, lactose, sucrose, maltose, trehalose, cellbiose, mannose, xylose, arabinose, glucoronic acid, galactoronic acid, mannuronic acid, glucosamine, galatosamine, and neuramic acid.

In some embodiments, nanocarriers can comprise one or more polymers. Polymers of a nanocarrier can associate to form a polymeric matrix. In some embodiments a mechanophore can be covalently linked with one or more polymers of the polymeric matrix. In some embodiments, a mechanophore can be noncovalently associated with one or more polymers of the polymeric matrix. For example, a mechanophore can be encapsulated within, surrounded by, and/or dispersed throughout a polymeric matrix. A mechanophore can be associated with one or more polymers of a polymeric matrix by, for example, hydrophobic interactions, charge interactions, or van der Waals forces.

Polymers can be natural or unnatural (synthetic) polymers. Polymers can be homopolymers or copolymers comprising two or more monomers. Copolymers can be random, block, or comprise a combination of random and block sequences.

A polymer can comprise a polyester, polycarbonate, polyamide, or polyether, or unit thereof. A polymer can comprises poly(ethylene glycol) (PEG), polypropylene glycol, poly(lactic acid), poly(glycolic acid), poly(lactic-co-glycolic acid), or a polycaprolactone, or unit thereof. A polymer can be biodegradable. Additional examples of polymers include, polyethylenes, polycarbonates (e.g. poly(1,3-dioxan-2one)), polyanhydrides (e.g. poly(sebacic anhydride)), polypropylfumerates, polyamides (e.g. polycaprolactam), polyacetals, polyethers, polyesters (e.g., polylactide, polyglycolide, polylactide-co-glycolide, polycaprolactone, polyhydroxyacid (e.g. poly(8-hydroxyalkanoate)), poly(orthoesters), polycyanoacrylates, polyvinyl alcohols, polyurethanes, polyphosphazenes, polyacrylates, polymethacrylates, polyureas, polystyrenes, and polyamines, polylysine, polylysine-PEG copolymers, and poly(ethyleneimine), poly (ethylene imine)-PEG copolymers.

Polymers can be, e.g., polyesters, including copolymers comprising lactic acid and glycolic acid units, such as poly(lactic acid-co-glycolic acid) and poly(lactide-co-glycolide) (PLGA); and homopolymers comprising glycolic acid units (PGA) and lactic acid units, such as poly-L-lactic acid, poly-D-lactic acid, poly-D,L-lactic acid, poly-L-lactide, poly-D-lactide, and poly-D,L-lactide (PLA). Other polyesters include, for example, polyhydroxyacids; PEG copolymers and copolymers of lactide and glycolide (e.g., PLA-PEG copolymers, PGA-PEG copolymers, PLGA-PEG copolymers, and derivatives thereof). In some embodiments, polyesters include, for example, poly(caprolactone), poly (caprolactone)-PEG copolymers, poly(L-lactide-co-L-lysine), poly(serine ester), poly(4-hydroxy-L-proline ester), poly[α-(4-aminobutyl)-L-glycolic acid], and derivatives thereof.

A load of a nanocarrier is the amount of mechanophore coupled to or present within the nanocarrier based on the total dry recipe weight of materials in an entire nanocarrier (weight/weight). The load on average across nanocarriers can be about 0.1, 1.0, 5, 10, 20, 30, 40, 50, 60, 70, 80% or more on average across the population of nanocarriers.

Cells, Tissue, and Tumors

Provided herein is a method of killing cells, tissue, or tumors comprising delivering the mechanophore gelled compositions or mechanophore nanocarrier compositions described herein to the cells, tissue, or tumors and activating the azo-mechanophores, peroxide-mechanophores, or disulfide-mechanophores within the compositions with HIFU.

Mechanophore gelled compositions or mechanophore nanocarrier compositions described herein can be formulated for various routes of administration. Suitable routes of administration can, for example, include oral, sublingual, inhalation, rectal, transmucosal, transdermal, intracavernosal, topical, intestinal, or parenteral delivery, including intramuscular, subcutaneous, and intramedullary injections as well as intrathecal, direct intraventricular, intravenous, intraperitoneal, intranasal, or intraocular injections. In some embodiments, injections can be administered, proximate, or directly to the cells, tissue, or tumors. In some embodiments, the mechanophore gelled compositions or mechanophore nanocarrier compositions described herein can be directly placed on or near the cells, tissue, or tumor.

Cells can be e.g., neurons, stem cells, red blood cells, white blood cells, neutrophils, eosinophils, basophils, lymphocytes, platelets, nerve cells, neuroglial cells, muscle cells, skeletal muscle cells, cardiac muscle cells, atrial cells, ventricular cells, Prukinje cells, smooth muscle cells, cartilage cells, bone cells, osteoclasts, osteoblasts, osteocytes, lining cells, skin cells, endothelial cells, epithelial cells, fat cells, cancer cells, bacterial cells, or virus-infected cells.

Tissues include, for example, connective tissue (e.g., fat tissues, bone, tendon), muscle tissue (e.g., cardiac muscle tissue, smooth muscle tissue, skeletal muscle tissue), nervous tissue (e.g., brain tissue, spinal cord tissue, nerve tissue), and epithelial tissue (e.g., skin, simple squamous, simple cuboidal, simple columnar, pseudostratified columnar, stratified squamous keratinized, stratified squamous non-keratinized).

Other cells and tissues that can targeted include for example, joint, ligaments, tendons, glands, stomach, intestine, liver, gall bladder, pancreas, lungs, kidney, bladder, urethra, ovary, uterus, testes, prostrate, heart, arteries, veins, lymph node, bone marrow, spleen, spinal cord, a nerve cell body, a ganglion, a dorsal root ganglion, an afferent nerve fiber, an afferent nerve bundle, an afferent nerve ending, a sensory nerve fiber, a sensory nerve bundle, a sensory nerve ending, and a sensory receptor.

Tumors can occur anywhere in a body including connective tissue, endothelium, mesothelium, blood, lymphoid cells, muscle, epithelial tissues, neural tissue, Amine Precursor Uptake and Decarboxylation (APUD) system, gonads, and breast tissue. Tumors can be benign, premalignant, or malignant. Benign tumors can be e.g., fibroma, myxoma, lipoma, chondroma, osteoma, fibrous histiocytoma, hemangioma, hemangiopericytoma, lymphangioma, "Preleukemias", "myeloproliferative disorders," Plasmacytosis, leiomyoma, rhabdomyoma, Adenoma, ganglioneuroma, meningioma, or Fibroadenoma.

Malignant tumors can be e.g., fibrosarcoma, myxosarcoma, liposarcoma, chondrosarcoma, osteosarcoma, chordoma, malignant fibrous histiocytoma, hemangisarcoma, angiosarcoma, lymphangiosarcoma, mesothelioma, eukemia, aleukemic tumors, Plasmacytoma, multiple myeloma, Hodgkin lymphoma, Non-Hodgkin lymphoma, leiomysarcoma, rhabdomyosarcoma, Squamous cell carcinoma, epidermoid carcinoma, Adenocarcinoma, Hepatoma: hepatocellular carcinoma, Renal cell carcinoma, hypernephroma Cholangiocarcinoma, Choriocarcinoma, glioblastoma, neuroblastoma, medulloblastoma, malignant meningioma, or Cystosarcoma phylloides.

In some embodiments, the cells, tissues, or tumors can be cancerous.

Cancer is a group of diseases involving abnormal cell growth with the potential to invade or spread to other parts of the body. The term "cancer" refers to a group of diseases characterized by abnormal and uncontrolled cell proliferation starting at one site (primary site) with the potential to invade and to spread to other sites (secondary sites, metastases) which differentiate cancer (malignant tumors) from benign tumors. Virtually all the organs can be affected, leading to more than 100 types of cancer that can affect humans, for example.

Exemplary cancers described by the national cancer institute include: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood: Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma. Childhood Brain Stem; Glioma. Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's; Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplasia Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; and Wilms' Tumor.

In some embodiments, the cells, tissue, or tumors are cancerous and are present in a mammal.

A mammal can be, for example, a human, non-human primate, feline, canine, bovine, equine, rodent, or marsupial.

In some embodiments, the cells, tissue, or tumors are present in vitro. In some embodiments, the cells, tissues, or tumors are present in vivo.

In some embodiments, the method of killing cells, tissue, or tumors can comprise delivering the mechanophore gelled compositions or mechanophore nanocarrier compositions described herein to the cells and activating the azo-mechanophores, peroxide-mechanophores, or disulfide-mechanophores with HIFU. Free radicals are generated, which are converted to reactive oxygen species, which in turn kill the cells, tissue, or tumors via oxidative cytotoxicity, apoptosis, or both.

In some embodiments, the HIFU can penetrate into a body, tissue, or tumors to a depth of more than 1 cm (e.g., about 0.1, 0.5, 1.0, 1.5, 2.0, 2.5, 3.0, 3.5, 4.0, 4.5, 5.0, 5.5, 6.0, 6.5, 7.5, 8.0, 8.5, 9.0, 9.5, 10.0 or more cm) or any range between about 0.1 and 10.0 cm (e.g., more than about 1.0 to about 8.0 cm, more than about 2.0 to about 5.0 cm).

Cancer Therapies

In some embodiments, the method can comprise delivering one or more additional cancer therapies to the mammal in addition to the method of killing cells, tissue, or tumors comprising delivering the mechanophore gelled compositions or mechanophore nanocarrier compositions described herein to the cells and activating the azo-mechanophores, peroxide-mechanophores, or disulfide-mechanophores with HIFU.

Cancer therapies can include any method that can be used to treat, ameliorate, or lessen the symptoms of cancer or a tumor or that can reduce the amount or cancerous cells or the amount or size of tumors. Treatments can include surgery, radiotherapy, chemotherapy, targeted therapy, immunotherapy, or any combination thereof. In some aspects, administration can be in combination with one or more additional therapeutic agents. The phrases "combination therapy", "combined with" and the like refer to the use of more than one treatment simultaneously to increase the response. Such therapies can be administered prior to, simultaneously with, or following administration of one another.

The term "chemotherapy" or "chemotherapeutic agent" as used herein refers to any therapeutic agent used to treat cancer. Examples of chemotherapeutic agents include, but are not limited to, (i) anti-microtubules agents comprising *vinca* alkaloids (vinblastine, vincristine, vinflunine, vindesine, and vinorelbine), taxanes (cabazitaxel, docetaxel, larotaxel, ortataxel, paclitaxel, and tesetaxel), epothilones (ixabepilone), and podophyllotoxin (etoposide and teniposide); (ii) antimetabolite agents comprising anti-folates (aminopterin, methotrexate, pemetrexed, pralatrexate, and raltitrexed), and deoxynucleoside analogues (azacitidine, capecitabine, carmofur, cladribine, clofarabine, cytarabine, decitabine, doxifluridine, floxuridine, fludarabine, fluorouracil, gemcitabine, hydroxycarbamide, mercaptopurine, nelarabine, pentostatin, tegafur, and thioguanine); (iii) topoisomerase inhibitors comprising Topoisomerase I inhibitors (belotecan, camptothecin, cositecan, gimatecan, exatecan, irinotecan, lurtotecan, silatecan, topotecan, and rubitecan) and Topoisomerase II inhibitors (aclarubicin, amrubicin, daunorubicin, doxorubicin, epirubicin, etoposide, idarubicinm, merbarone, mitoxantrone, novobiocin, pirarubicin, teniposide, valrubicin, and zorubicin); (iv) alkylating agents comprising nitrogen mustards (bendamustine, busulfan, chlorambucil, cyclophosphamide, estramustine phosphate, ifosamide, mechlorethamine, melphalan, prednimustine, trofosfamide, and uramustine), nitrosoureas (carmustine (BCNU), fotemustine, lomustine (CCNU), N-Nitroso-N-methylurea (MNU), nimustine, ranimustine semustine (MeCCNU), and streptozotocin), platinum-based (cisplatin, carboplatin, dicycloplatin, nedaplatin, oxaliplatin and satraplatin), aziridines (carboquone, thiotepa, mytomycin, diaziquone (AZQ), triaziquone and triethylenemelamine), alkyl sulfonates (busulfan, mannosulfan, and treosulfan), non-classical alkylating agents (hydrazines, procarbazine, triazenes, hexamethylmelamine, altretamine, mitobronitol, and pipobroman), tetrazines (dacarbazine, mitozolomide and temozolomide); (v) anthracyclines agents comprising doxorubicin and daunorubicin. Derivatives of these compounds include epirubicin and idarubicin; pirarubicin, aclarubicin, and mitoxantrone, bleomycins, mitomycin C, mitoxantrone, and actinomycin; (vi) enzyme inhibitors agents comprising FI inhibitor (Tipifarnib), CDK inhibitors (Abemaciclib, Alvocidib, Palbociclib, Ribociclib, and Seliciclib), PrI inhibitor (Bortezomib, Carfilzomib, and Ixazomib), PhI inhibitor (Anagrelide), IMPDI inhibitor (Tiazofurin), LI inhibitor (Masoprocol), PARP inhibitor (Niraparib, Olaparib, Rucaparib), HDAC inhibitor (Belinostat, Panobinostat, Romidepsin, Vorinostat), and PIKI inhibitor (Idelalisib); (vii) receptor antagonist agent comprising ERA receptor antagonist (Atrasentan), Retinoid X receptor antagonist (Bexarotene), Sex steroid receptor antagonist (Testolactone); (viii) ungrouped agent comprising Amsacrine, Trabectedin, Retinoids (Alitretinoin Tretinoin) Arsenic trioxide, Asparagine depleters (Asparaginase/Pegaspargase), Celecoxib, Demecolcine Elesclomol, Elsamitrucin, Etoglucid, Lonidamine, Lucanthone, Mitoguazone, Mitotane, Oblimersen, Omacetaxine mepesuccinate, and Eribulin.

The term "immunotherapy" refers to any type of therapy that ameliorates, treats, or prevents a malignancy in a subject by assisting or boosting the subject's immune system in eradicating cancerous cells. Modulating the immune system includes inducing, stimulating or enhancing the immune system as well as reducing, suppressing or inhibiting the immune system. Immunotherapy can be active or passive. Passive immunotherapy relies on the administration of drugs, such as monoclonal antibodies directed against the target to eliminate it. For example, tumor-targeted monoclonal antibodies have demonstrated clinical efficacy to treat cancer. Active immunotherapy aims to induce cellular immunity and establish immunological memory against the target agent. Active immunotherapy includes, but is not limited to, vaccination, and immune modulators.

Types of immunotherapy include, for example, immune checkpoint inhibitors, T-cell transfer therapy (i.e., adoptive cell therapy, adoptive immunotherapy, or immune cell therapy), monoclonal antibodies (e.g., monoclonal antibodies that can mark cancer cells so that they will be better identified and destroyed by the immune system), treatment vaccines (e.g., Sipuleucel-T, T-VEC), and immune system modulators (e.g., cytokines, interferons, interleukins (e.g., IL-2; IL-11), granulocyte-macrophage colony-stimulating factor (GM-CSF) and granulocyte colony-stimulating factor (G-CSF), BCG, and immunomodulatory drugs such as thalidomide, lenalidomide, pomalidomide, imiquimod.

"Checkpoint inhibitor therapy" is a form of cancer treatment that uses immune checkpoints which affect immune system functioning. Immune checkpoints can be stimulatory or inhibitory. Tumors can use these checkpoints to protect themselves from immune system attacks. Checkpoint therapy can block inhibitory checkpoints, restoring immune system function. Checkpoint proteins include programmed cell death 1 protein (PDCD1, PD-1; also known as CD279) and its ligand, PD-1 ligand 1 (PD-L1, CD274), cytotoxic T-lymphocyte-associated protein 4 (CTLA-4), A2AR (Adenosine A2A receptor), B7-H3 (or CD276), B7-H4 (or VTCN1), BTLA (B and T Lymphocyte Attenuator, or CD272), IDO (Indoleamine 2,3-dioxygenase), KIR (Killer-cell Immunoglobulin-like Receptor), LAG3 (Lymphocyte Activation Gene-3), TIM-3 (T-cell Immunoglobulin domain and Mucin domain 3), and VISTA (V-domain Ig suppressor of T cell activation).

Targeted therapies (also called targeted cancer therapies herein) are drugs or other substances (e.g., siRNA) that block the growth and spread of cancer by interfering with specific molecular targets that are involved in the growth, progression, and spread of cancer. Targeted therapies differ from standard chemotherapy in several ways including that they act on specific molecular targets that are associated with cancer, whereas most standard chemotherapies act on all rapidly dividing normal and cancerous cells. Examples of a targeted therapies include HIF-2α inhibitors such as PT2385/PT2399.

Tumor-Hominq Compounds

Tumor-homing compounds are compounds that selectively home to tumors and tumor-associated tissue. Many compounds that target, bind to, and/or home to tumors are known, most of which can be used as tumor-homing compounds in the disclosed compositions. Tumor-homing compounds can each be independently selected from any known tumor-homing compounds. Tumor-homing compounds can be non-covalently or covalently linked to any gelled mechanophore compositions or mechanophore nanocarrier compositions described herein.

Tumor-homing compounds can comprise, for example, KRGARST (SEQ ID NO: 14), the amino acid sequence AKRGARSTA (SEQ ID NO: 15), or a conservative derivative thereof, the amino acid sequence CKRGARSTC (SEQ ID NO: 16) or a conservative derivative thereof, or any combination thereof, including peptidomimetics thereof.

Useful peptides for tumor targeting include, for example, the tumor-homing CendR peptide iRGD, LyP-1, a peptide that contains a putative CendR element and has tumor-penetrating properties, and RGR peptides. The LyP-1 peptide has a unique target within tumors; it can accumulate in the hypoxic/low nutrient areas of tumors (Laakkonen et al. "A tumor-homing peptide with a targeting specificity related to lymphatic vessels." *Nature medicine* 8(7):751-755(2002); Laakkonen et al. "Antitumor activity of a homing peptide that targets tumor lymphatics and tumor cells." *Proceedings of the National Academy of Sciences* 101.25 101:9381-9386 (2004); Karmali et al., "Tissue-penetrating delivery of compounds and nanoparticles into tumors." *Cancer cell* 16(6)" 510-520 (2009)). CRGRRST (RGR; SEQ ID NO: 17; Joyce et al., "Stage-specific vascular markers revealed by phage display in a mouse model of pancreatic islet tumorigenesis." *Cancer cell* 4(5): 293-403 (2003)) is a peptide that has been successfully used in targeting a cytokine antibody combination into tumors (Hamzah et al., "Specific penetration and accumulation of a homing peptide within atherosclerotic plaques of apolipoprotein E-deficient mice." *Proceedings of the National Academy of Sciences* 108(17): 7154-7159 (2008)). This peptide is linear, which simplifies the synthesis. Like LyP-1, RGR is at least to some extent tumor type-specific (Joyce et al., "Stage-specific vascular markers revealed by phage display in a mouse model of pancreatic islet tumorigenesis." *Cancer cell* 4(5): 293-403 (2003)), but the tumor types recognized by the two peptides seem to be partially different, which may be an advantage in testing combinations with the pan-tumor iRGD.

Because tumors can include clot-related proteins, clot-binding and clot-homing compounds can also be tumor-homing compounds. Such tumor-homing clot-binding compounds can be used as tumor-homing compounds as described herein. Tumor-homing compounds can each be independently selected from, for example, an amino acid segment comprising the amino acid sequence REK, an amino acid segment comprising the amino acid sequence CAR (such as CARSKNKDC; SEQ ID NO: 18), an amino acid segment comprising the amino acid sequence CRK (such as CRKDKC; SEQ ID NO: 19), a fibrin-binding peptide, a peptide that binds clots and not fibrin (such as CGLIIQKNEC (CLT1; SEQ ID NO: 20) and CNAGESSKNC (CLT2; SEQ ID NO: 21)), a clot-binding antibody, and a clot-binding small organic molecule. A plurality of the clot-binding compounds can each independently comprise an amino acid segment comprising the amino acid sequence REK. Such peptides are also described in U.S. Patent Application Publication No. 2008/0305101. Peptides comprising amino acid sequences CAR or CRK are also described in U.S. Patent Application Publication No. 2009/0036349.

LyP-1 are homing molecules that selectively home to tumor lymphatic vasculature, for example, the lymphatic vasculature of breast cancer tumors and osteosarcomas, in preference to normal lymphatic vasculature. LyP-1 can selectively home, for example, to the lymphatic vasculature of squamous carcinomas. The core LyP-1 peptide has an amino acid sequence CGNKRTRGC (SEQ ID NO: 22). LyP-1 peptides are described in U.S. Patent Application Nos. 2004/0087499, 2007/0219134, and 2008/0014143.

A tumor-homing clot-binding compound can also comprise a fibrin-binding peptide (FBP). Examples of fibrin-binding peptides are described in Van Rooijen & Sanders, "Liposome mediated depletion of macrophages: mechanism of action, preparation of liposomes and applications." *Journal of immunological methods* 174(1-2): 83-93 (1994); Moghimi et al., "Long-circulating and target-specific nanoparticles: theory to practice." *Pharmacological reviews* 53(2): 283-318 (2001); U.S. Pat. No. 5,792,742).

Compositions and methods are more particularly described below and the Examples set forth herein are intended as illustrative only, as numerous modifications and variations therein will be apparent to those skilled in the art. The terms used in the specification generally have their ordinary meanings in the art, within the context of the compositions and methods described herein, and in the specific context where each term is used. Some terms have been more specifically defined herein to provide additional guidance to the practitioner regarding the description of the compositions and methods.

As used herein, the term "and/or" includes any and all combinations of one or more of the associated listed items. As used in the description herein and throughout the claims that follow, the meaning of "a", "an", and "the" includes plural reference as well as the singular reference unless the context clearly dictates otherwise. The term "about" in association with a numerical value means that the value varies up or down by 5%. For example, for a value of about 100, means 95 to 105 (or any value between 95 and 105).

All patents, patent applications, and other scientific or technical writings referred to anywhere herein are incorporated by reference herein in their entirety. The embodiments illustratively described herein suitably can be practiced in the absence of any element or elements, limitation or limitations that are specifically or not specifically disclosed herein. Thus, for example, in each instance herein any of the terms "comprising," "consisting essentially of," and "consisting of" can be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the claims. Thus, it should be understood that although the present methods and compositions have been specifically disclosed by embodiments and optional features, modifications and variations of the concepts herein disclosed can be resorted to by those skilled in the art, and that such modifications and variations are considered to be within the scope of the compositions and methods as defined by the description and the appended claims.

Any single term, single element, single phrase, group of terms, group of phrases, or group of elements described herein can each be specifically excluded from the claims.

Whenever a range is given in the specification, for example, a temperature range, a time range, a composition, or concentration range, all intermediate ranges and subranges, as well as all individual values included in the ranges given are intended to be included in the disclosure. It will be understood that any subranges or individual values in a range or subrange that are included in the description herein can be excluded from the aspects herein. It will be understood that any elements or steps that are included in the description herein can be excluded from the claimed compositions or methods.

In addition, where features or aspects of the compositions and methods are described in terms of Markush groups or other grouping of alternatives, those skilled in the art will recognize that the compositions and methods are also thereby described in terms of any individual member or subgroup of members of the Markush group or other group.

Materials and Methods for Examples 1-5

Chemicals

PEG diacrylate (molecular weight ca. 575) and 4,4'-azobis (4-cyanovaleric acid) (ACVA) were purchased from Sigma Aldrich and stored in a freezer. The azo-PEG copolymer macroinitiator, i.e., the polyester of PEG diol (molecular weight ca. 2000) and ACVA with overall molecular weight of 15,000-30,000 was purchased from Fujifilm Wako and stored in a freezer. Potassium carbonate, phosphate buffer solution (PBS, pH=7.4), luminol, potassium ferricyanide, potassium hydroxide and hydrogen peroxide were purchased from Fisher Scientific. The Pierce quantitative peroxide assay kit for ROS detection based on xylenol orange (XO) and iron (II) was purchased from Thermo Scientific and stored in a fridge. Except for PEG diacrylate that was thaw and passed through a basic alumina plug to remove the inhibitors prior to use, other chemicals were used without further purification.

The Synthesis of Mechanophore-PEG Hydrogel and the Thermal Stability of Azo-Mechanophore The synthesis of azo-mechanophore based PEG hydrogel is described in more detail below and illustrated in FIG. 6. Briefly, the azo groups in azo-PEG macroinitiator partially decomposed to initiate the free-radical (FR) crosslinking reaction, which crosslinks the azo-PEG copolymers to form the hydrogel. According to the thermal decomposition kinetics (FIG. 3A and Table 1), ca. 86% of azo groups remains intact, which become mechanophores embedded into the PEG hydrogel. Mechanophore-free hydrogels were also synthesized as described below. After the gel formation, any free polymer, crosslinker or ROS that are not bound to the polymer network were removed during purification.

TABLE 1

Summarization of azo-mechanoohore decomposition.

| Sample | T (° C.) | t | Decomposition (%) |
|---|---|---|---|
| Mechanophore hydrogel preparation | 65 | 2 hours | 13.9 |
| HIFU-induced heating  One spot | <60 | 10 seconds | <0.01 |
| HIFU-induced heating  Full MDT | <60 | 200 seconds | <0.2 |
| Physiological conditions | 37 | 24 hours | 2.4 |
| Room temperature | 25 | 24 hours | 0.3 |
| Fridge storage | 4 | 1 year | 1.7 |

The thermal decomposition rate of azo-mechanophores were calculated from the decomposition kinetics of the azo-PEG macroinitiator according to first order reaction kinetics equation:

$$\frac{[A]}{[A]_o} = e^{-kt}. \quad [1]$$

where [A] and $[A]_o$ are the amount of current and initial of azo groups respectively, t is the decomposition time, and k is the temperature dependent rate constant that follows Arrhenius equation:

$$k = Ae^{-\frac{E_a}{RT}}. \quad [2]$$

where A is the pre-exponential factor, $E_a$ is the activation energy, R is the universal gas constant, and T is the temperature in kelvins. For the azo group in azo-PEG macroinitiator, $A=1.18\times10^{16}$ s$^{-1}$ and $E_a=134.4$ kJ mol$^{-1}$ (provided by the manufacture, Fujifilm Wako), which are similar to its small molecular analog ACVA ($A=6.21\times10^{15}$ s$^{-1}$ and $E_a=132.9$ kJ mol$^{-1}$). A few key data was calculated and summarized in Table 1.

Preparation of Azo-Mechanophore PEG Hydrogels and Control Hydrogels.

Figure 6:
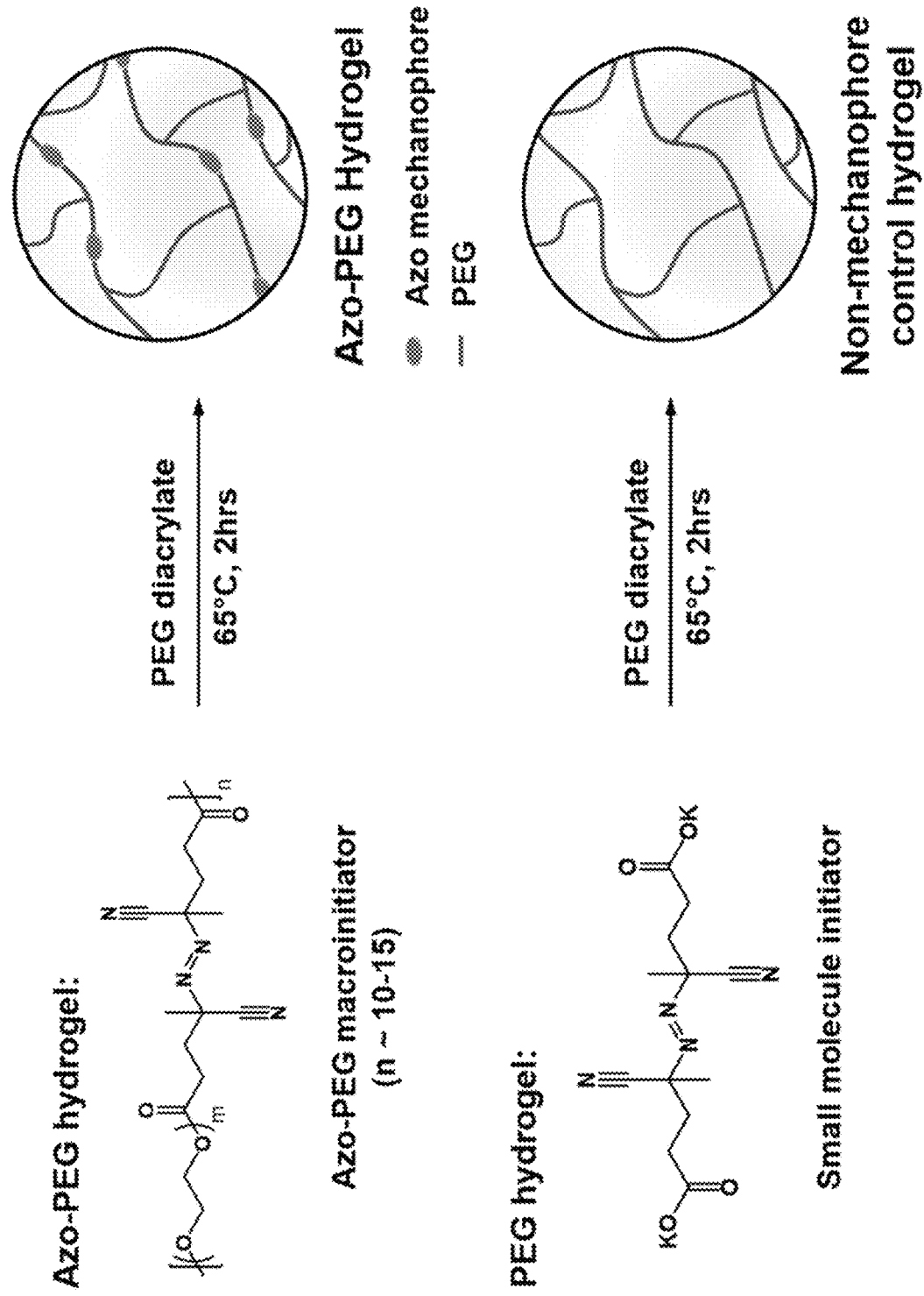
FIG. 6 shows synthesis and structure of azo-mechanophore hydrogels and non-mechanophore control hydrogels.

PEG hydrogels with azo-mechanophores were synthesized using an azo-PEG macroinitiator with PEG diacrylate crosslinker (FIG. 6). In a 40 mL vial, 3.2 g of macroinitiator and 4.8 g of PEG diacrylate were dissolved in 24 mL phosphate-buffer saline (PBS, pH=7.4) under vigorous agitation by a vortex mixer. The solution was transferred to a 6-well cell culturing plate (well area 9.6 cm$^2$) at a volume of 5 mL per well. The plate was sealed and heated by an oven at 65° C. for 2 hours to cure the hydrogel. After cooling down, the hydrogels were cut into cylindrical samples with diameter of 1.6 cm and thickness of ~4 mm. All samples were purified by soaking in PBS at 4° C. for at least 3 days (buffer replaced daily) to remove any reactive ROS generated during hydrogel curing. The control hydrogel without azo-mechanophores were prepared similarly, with 4.8 g of PEG diacrylates, 320 mg (1.14 mmol) of ACVA and 160 mg (1.16 mmol) of K2CO3 were dissolved in 24 mL PBS, followed by curing, cutting and purification under the same condition. Because ACVA is a small molecule, the azo group did not incorporate into the polymer and were removed during purification.

The Chemical Reaction of Free Radicals (FRs)

Figure 7:
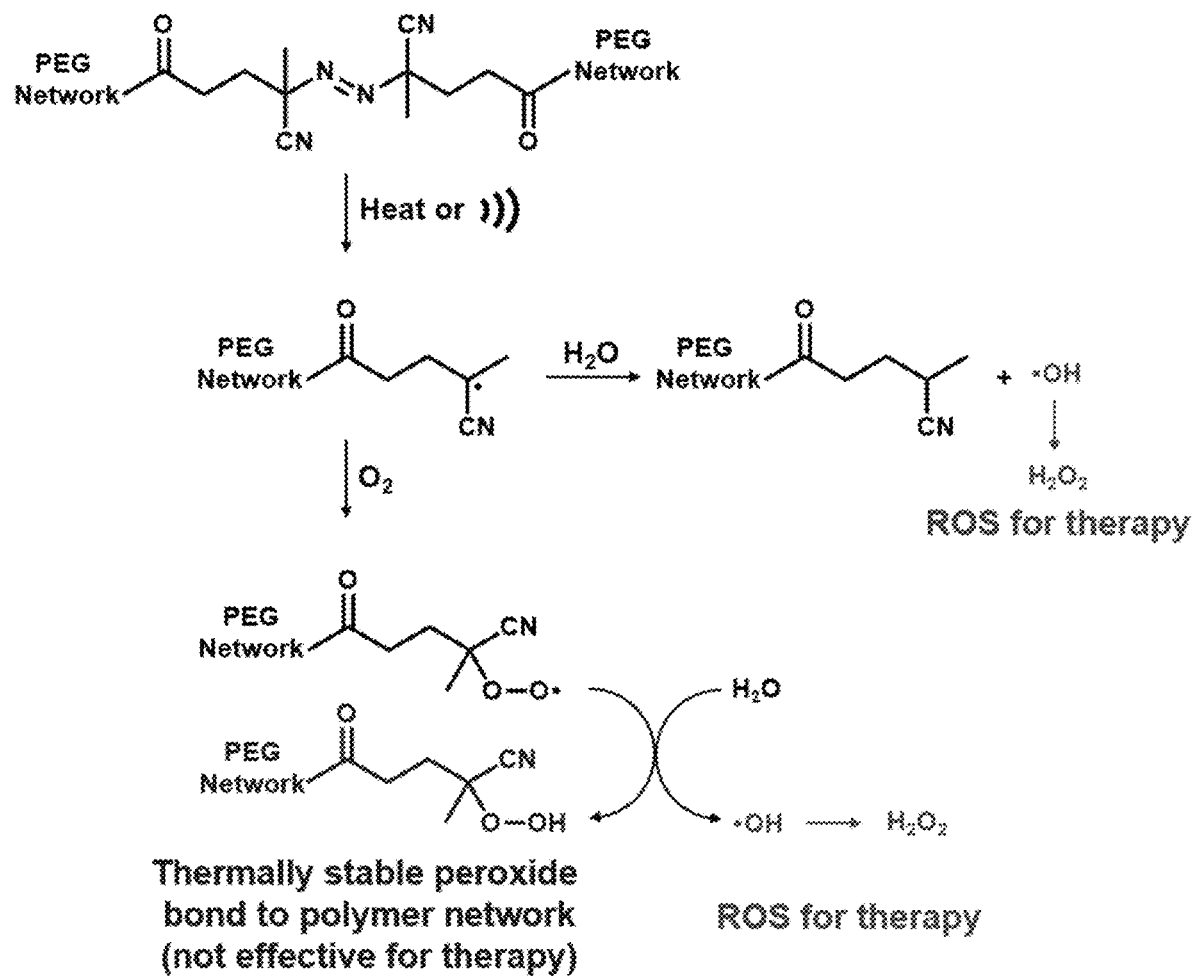
FIG. 7 shows the proposed mechanism for the formation of ROS (e.g. $H_2O_2$ and hydroxyl radicals) and stable peroxides bound to polymer network.

A large amount FRs was generated during the hydrogel synthesis based on FR chemistry. In the presence of oxygen, some FRs was converted to thermally stable peroxides, such as organic hydroperoxides as shown in FIG. 7. These stable peroxides were covalently bound to the hydrogel network. Therefore, they were not removed during the purification process, but are inactive for radical reactions or therapy. For mechanophore activation, however, most mechanically generated FRs are converted into highly reactive species including hydroxyl radicals and $H_2O_2$.

Validation of ROS Formation by Luminal Chemiluminescence and Xylenol Orange (XO) Colorimetric Tests For chemiluminescence detection, luminol and iron solutions were prepared by dissolving luminol (90 mg, 0.51 mmol) and $K_3Fe(CN)_6$ (15 mg, 0.046 mmol) in two vials of 25 mL of 0.03M KOH solution (25 mL), respectively. The hydrogels were immersed in the luminol solution for 20 minutes prior to sonication. After sonication, the samples were immediately immersed in the iron solution for chemiluminescence detection. For colorimetric detection, since $Fe^{2+}$/XO requires acidic condition, hydrogel samples were further purified by soaking in deionized water for 1 day to remove the PBS buffer. A sonicated mechanophore hydrogel, a sonicated control hydrogel and a non-sonicated mechanophore hydrogel were soaked in 5 mL freshly prepared $Fe^{2+}$/XO solutions, respectively. After exactly 30 min of soaking, 1 mL of each solution was collected for UV-Vis study. The UV-Vis data was recorded by Shimadzu UV-2410PC UV-Vis recording spectrophotometer with disposable 10 mm pathlength semi-micro cuvettes.

HIFU Triggering System, Beam Characteristics, and Sonication Procedure

FIG. 8 shows a photograph of the designed HIFU setup for the mechanical triggering of azo-mechanophores in PEG hydrogels. To prevent the change in the mechanical properties of azo-mechanophores by water, we purchased a cone-shape water container where the degassed water was filled and sealed with an acoustic membrane (FIG. 2B). The other side of the container was assembled with a 550 kHz HIFU transducer (f-number of 1.4). The full width at half maximum (FWHM) beamwidth ($B_W$) and depth of field ($Z_F$) of the transducer were measured to be 3.8 and 37.3 mm, respectively. The output voltage signal was converted to acoustic pressure (p, ~1.9 MPa) using the hydrophone (sensitivity of 96.00 mV·MPa$^{-1}$, FUS Instruments, Canada). Together with the measured acoustic and mechanical properties of the PEG hydrogels (See Table 2), the measured p was used to calculate spatial peak temporal average intensity ($I_{SPTA}=p^2 \cdot (2 \cdot \rho \cdot c)^{-1}$, 115 W·cm$^{-2}$). Note that the calculated $I_{SPTA}$ is slightly overestimated because the pressure field generated by HIFU would be reflected at the PEG hydrogels depending on the acoustic impedance (Table 2). Also due to the limited size of hydrogel sample, it is hypothesized that acoustic radiation force ($F=2 \cdot \alpha \cdot c^{-1} \cdot I_{SPTA}$) is a form of a standing wave, which would magnify the pressure at the focal spot and thus result in facilitating the mechanophore activation and ROS generation. A detailed sonication procedure is illustrated in FIG. 8.

TABLE 2

The measured acoustic and mechanical properties of PEG hydrogels.

|  | PEG Hydrogel (w/mechanophores) | PEG Hydrogel (w/o mechanophores) |
|---|---|---|
| Speed of sound, c (m · s$^{-1}$) | 1536.3 ± 2.9 | 1546.8 ± 5.3 |
| Density, ρ (kg · m$^{-3}$) | 1037 ± 58 | 1040 ± 56 |
| Attenuation coefficient, α (dB · m$^{-1}$) | 140 ± 12 (1 MHz) | 88 ± 22 (1 MHz) |
|  | 1163 ± 92 (10 MHz) | 497 ± 252 (10 MHz) |
| Acoustic impedance, $Z_o$ (MPa · s · m$^{-1}$) | 1.593 | 1.608 |

Temperature Measurement for HIFU Induced Heating

Figure 9A:
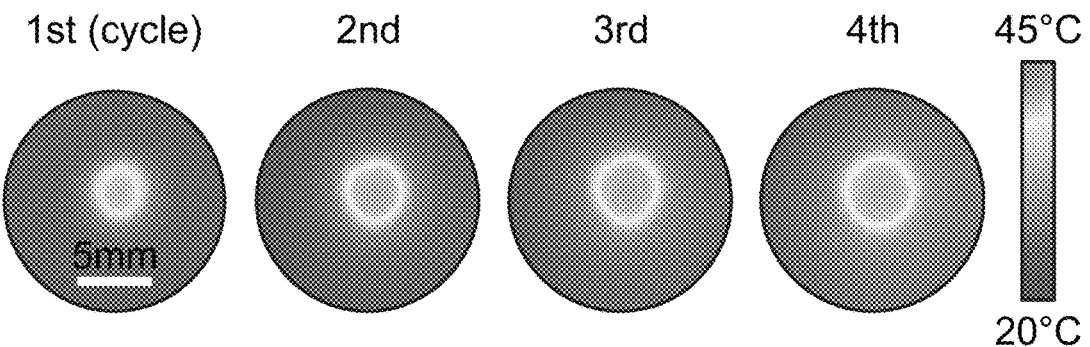
FIGS. 9A-9C show temperature measurement for HIFU induced heating.
Figure 9B:
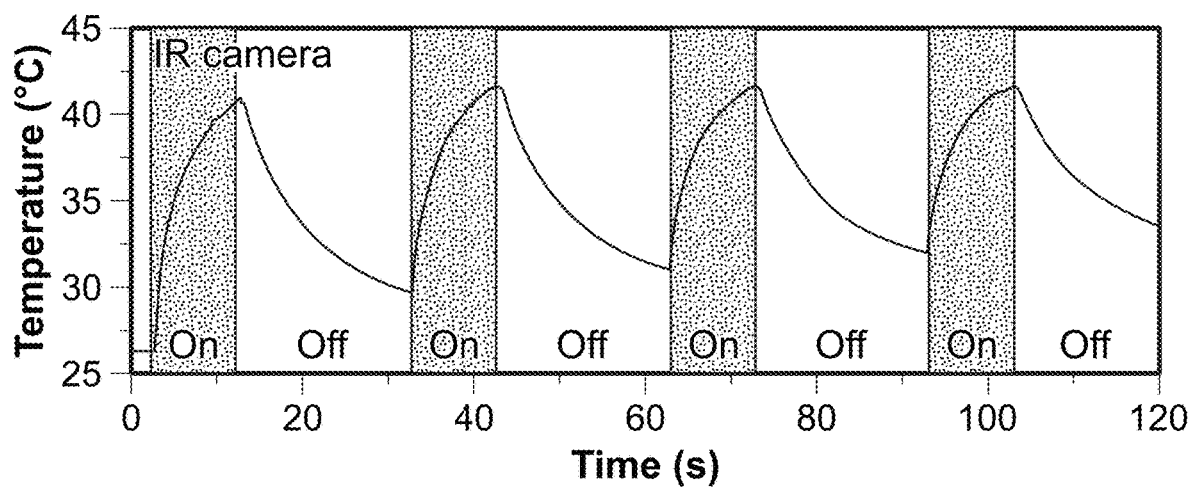
Figure 9C:
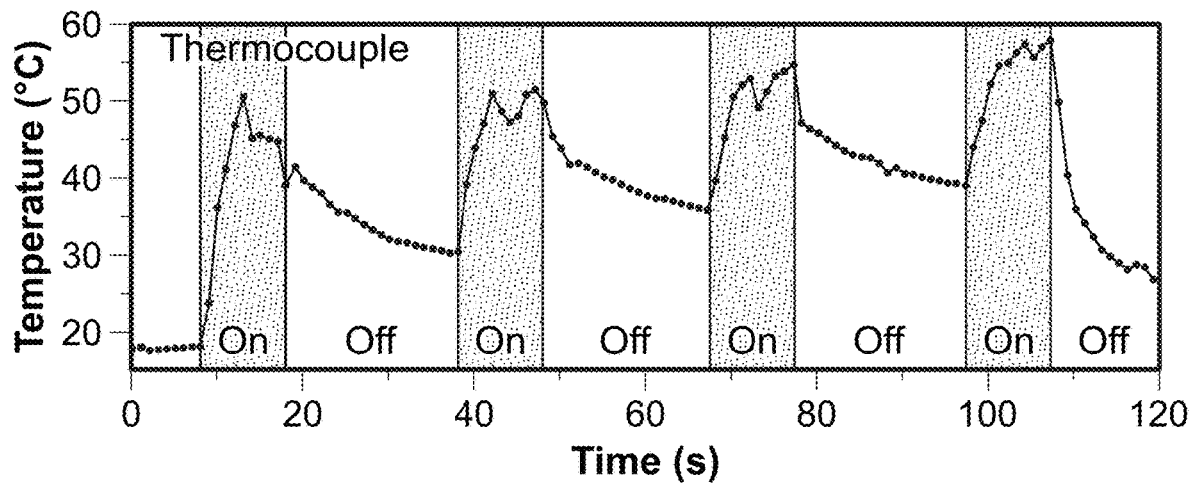

During a sonication period (10 s-on, 20 s-off, 4 cycles per spot), both the thermal infrared (IR) camera and thermocouple were employed to track the surface temperature and the temperature in the focal region, respectively. The IR camera image was recorded by a FLIR T1020 IR camera with a 50 μm close-up lens and a focal distance=9.7 cm, emissivity=1.0, ambient/reflected temperature=20° C., humidity=50% and frame rate=30 fps. Data was processed by Research IR Max 4 software (FLIR). (FIGS. 9 A and B). A thermocouple was connected to the computer to automatically record temperature in the focal region (FIG. 9C). We found temperatures recorded by the IR camera was lower than temperatures recorded by the thermocouple by ~12° C. due to heat dissipation along the height. Both observations indicate that the applied $I_{SPTA}$ (~115 W·cm$^{-2}$) is desirable to avoid the heat-induced mechanophore activation. This confirmed that mechanical force, i.e., acoustic radiation force, is dominant in the ROS generation from azo-mechanophores. Due to good thermal stability of the azo-mechanophore and limited HIFU-induced heating, cytotoxicity is not observed for both melanoma (B16F10) and breast cancer (E0771) cells, as demonstrated in the main manuscript and FIG. S7.

Acoustic and Mechanical Properties of Mechanophore-Embedded PEG Hydrogels

Figures 11A, 11B, 11C:
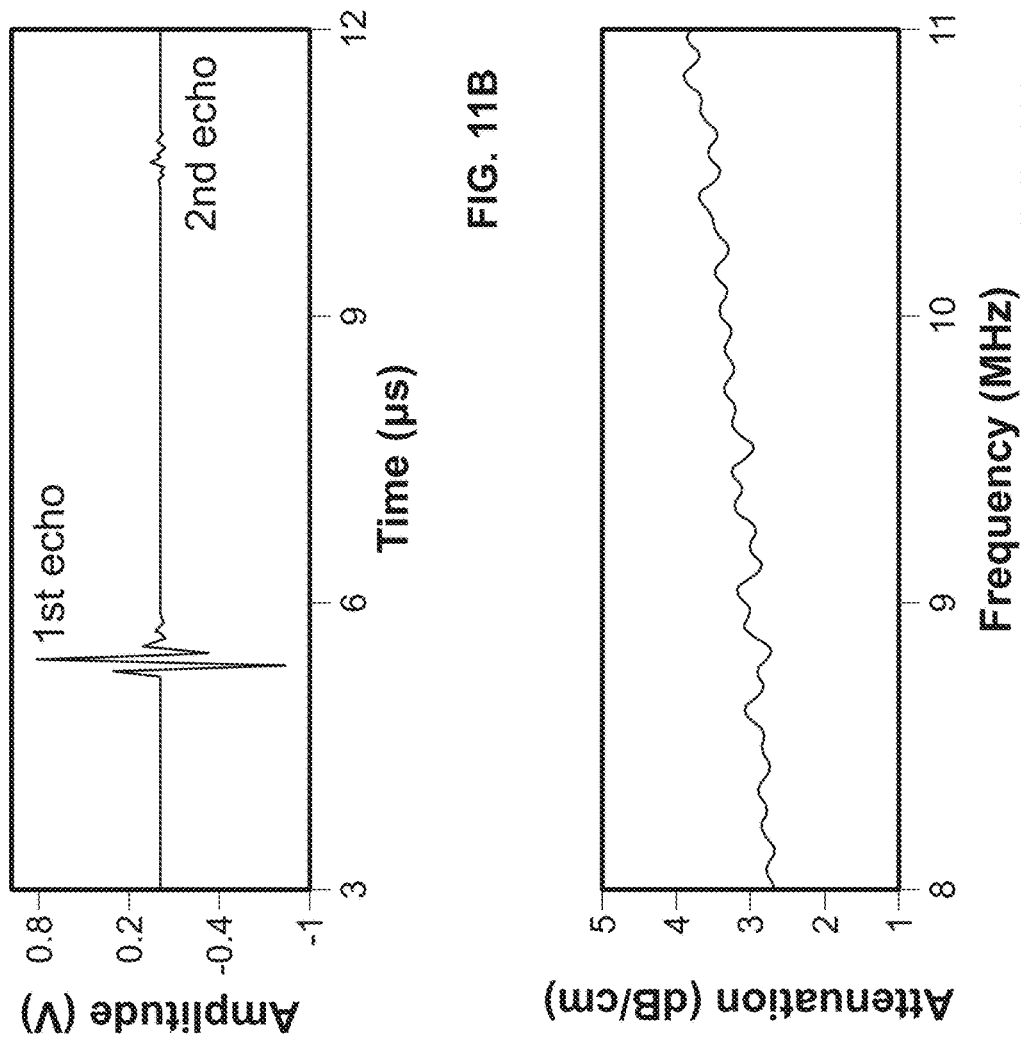
FIGS. 11A-11C show HIFU setup with a custom LabVIEW program on a personal computer.

To better understand the effect of azo-mechanophores on the mechanical properties of PEG hydrogels, speed of sound (c) and attenuation coefficient (a) were measured as described in Table 2. A previously developed ultrasonic setup was used to measure both parameters as shown in FIG. 11A. An Olympus 5800 pulser/receiver was used to generate pulse-echo mode signal with a 1 kHz pulse repetition frequency (PRF), and the generated signal was fed to a focused transducer: 1 MHz and 10 MHz for α; and 10 MHz for c. Using the time-of-flight (TOF) method (FIG. 11B), c of both PEG hydrogel with and without mechanophores was estimated. The measured value was approximately 1536.3 and 1546.8 m·s$^{-1}$, confirming no significant change in the acoustic properties of the samples by the addition of mechanophores. Based upon a pulse-echo insertion loss method, α was estimated:

$$\alpha(f) = 10 \cdot (2 \cdot d)^{-1} \cdot \log_{10}(P_r(f) \cdot P_s(f)^{-1}). \quad [1]$$

where d is the thickness (0.43 cm for sample with mechanophores and 0.33 cm for sample without mechanophores), $P_r(f)$ and $P_s(f)$ are the power spectrum of the reflected waveform (4, 5). As shown in FIG. 11C, the estimated spectral log difference, $\log_{10}(P_r(f) \cdot P_s(f)^{-1})$ fits in a linear trend within the effective bandwidth, enabling the calculation of a for each sample (for 1 MHz and 10 MHz respectively). Other properties estimated in this study, e.g., density, ρ and acoustic impedance, $Z_o$ (=ρ·c) were summarized in Table 2.

HIFU Setup for MDT

Figure 8B:
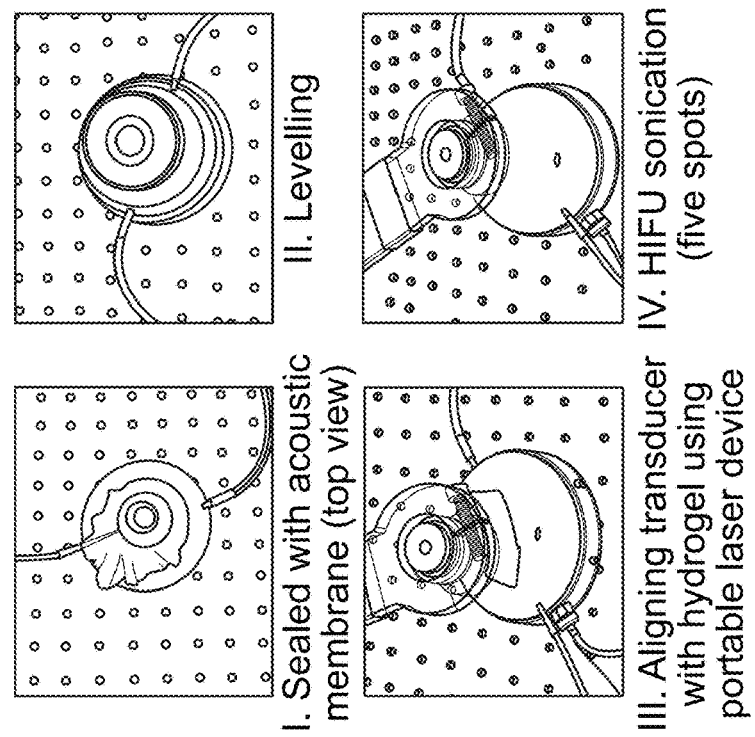
FIGS. 8A-8B show HIFU triggering system for the activation of azo-mechanophore hydrogels.
Figure 8A:
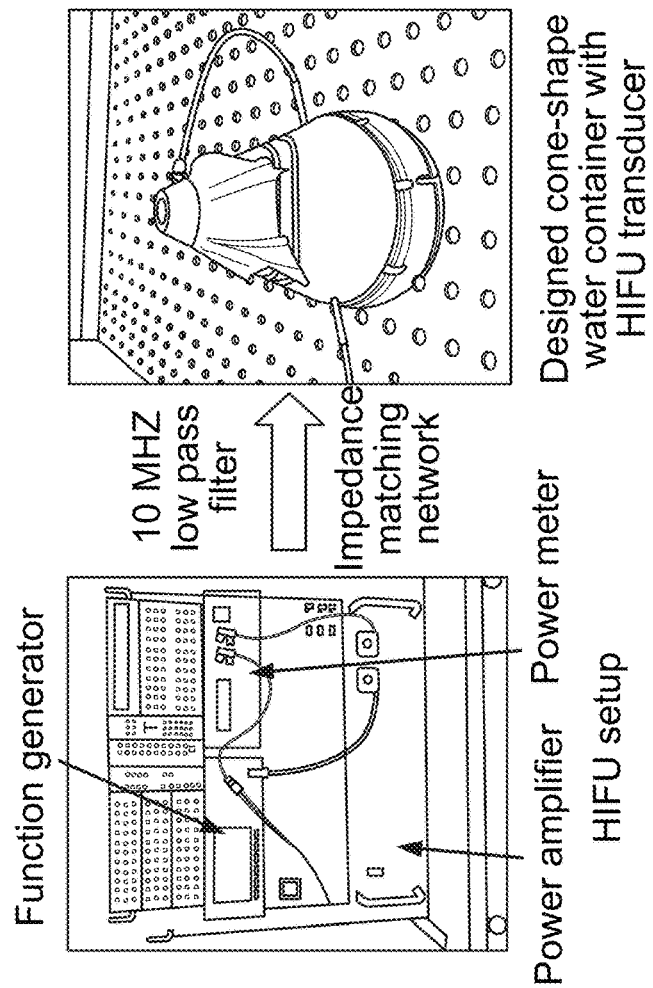

Having determined beam characteristics including full width at half maximum (FWHM) beamwidth ($B_W$) and depth of field ($Z_F$), etc., a CW-HIFU triggering system was developed (FIG. 2B). A mechanical irradiation of the mechanophore hydrogels could be interfered by coupling with water. To prevent this, we used a cone-shaped water container assembled with HIFU transducer (FIG. 2B, FIG. 8). A sinusoidal voltage signal was generated with a function generator (33500B, Keysight Technologies, Santa Rosa, CA) then sent to a 550 kHz spherically-focused HIFU transducer (f-number 1.4, FUS Instruments, Canada) through a 10 MHz low pass filter and an impedance matching network. The cone-shape container was filled with degassed water using tubes (FIG. 8A). All control and azo-mechanophore hydrogels were located on top of the container. Note that the interface between hydrogels and water was sealed with an acoustic membrane (FIG. 8B). Then the transducer was translated to expose five spots with ~4 mm interval between spots. The designed cone-shape water container assembled with HIFU setup is shown in FIG. 8A. The interface between water and the samples was completely sealed with an acoustic membrane. This ensured no changes in the mechanical properties of PEG hydrogels due to the contact with water. The geometry of this assembly was designed to avoid any reflection of the pressure field in the longitudinal direction, and the focal spot was located approximately 2 mm away from the acoustic membrane (FIG. 2B), making the focal spot located at half the thickness of the sample. In addition, a 550 kHz HIFU transducer (f-number of 1.4, FUS Instruments, Canada) was selected based upon the ratio of the beamwidth at the focal spot (~3.8 mm) to the sample diameter (16 mm). This configuration enabled the most efficient stress development for the mechanophore activation in the PEG hydrogel network. It is worthwhile to note that although the boundary reflected waves caused by the limited sample size would cause a standing wave in the sample and make it difficult to estimate the actual radiation force applied to the mechanophore particles, this would facilitate the mechanophore activation and thus the ROS generation. The entire HIFU setup was controlled using a custom LabVIEW program on a personal computer (FIG. 11), capable of temporal control of the sonication time and the input parameters. We first considered the conversion of output voltage of the beam (at the focal spot) to the acoustic pressure using a calibrated hydrophone (sensitivity of 96.00 mV·MPa$^{-1}$, FUS Instruments, Canada) then the corresponding $I_{SPTA}$ and F. We then determined the range of sonication time (10 s-on, 20 s-off, 4 cycles per spot) and $I_{SPTA}$ (115 W·cm$^{-2}$) after the observation of no visible damage on the surface. We also confirmed noticeable surface damage at $I_{STPA}$ above 135 W·cm$^{-2}$ with characteristics of thermal ablation. To achieve an optimum transfer of mechanical energy, five different sonication spots were considered (FIG. 2B). As described in FIG. 2B, the center of a sample was mounted on membrane of the HIFU assembly then the position of sample was changed along the horizontal direction for five different focal spots. A portable laser device placed over the sample was employed to achieve a better alignment between the HIFU assembly and samples.

In Vitro MDT Challenge Assay

Figures 12A, 12B:
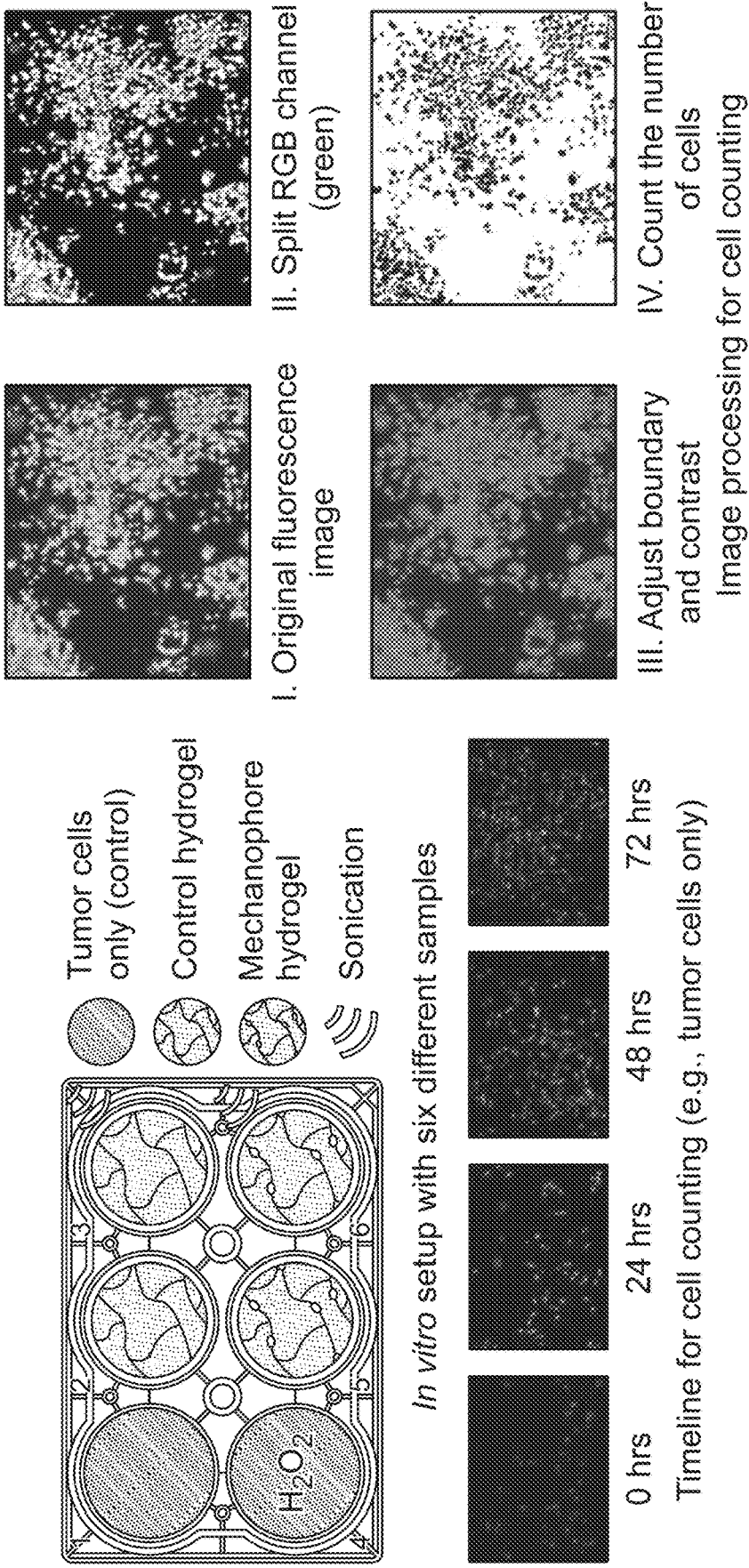
FIGS. 12A-12B show Live cells positively stained by Calcein-AM were counted using FIJI (NIH) and averaged over 4 counting fields per well at each time point.

B16F10 mouse skin melanoma cells were maintained in DMEM (Gibco) supplemented with 10% fetal bovine serum (FBS, Corning), penicillin and streptomycin (Thermo Fisher). B16F10 cells were a generous gift from Dr. Edward Roy at the University of Illinois at Urbana-Champaign. E0771 mouse breast cancer cells (CH3 BioSystems) were maintained in RPMI-1640 (Gibco) supplemented with 10% FBS (Corning), penicillin and streptomycin (Thermo Fisher). For free-radical challenge experiments, 0.05% trypsin dissociated cells were counted and $1 \times 10^4$ cells per well were seeded in cell culture-treated 6 well plates (Thermo Fisher) 24 hours before the start of the experiment. After sonication, the mechanophore-containing hydrogels were placed in 100 μm mesh cell strainers (Thermo Fisher) and inserted into the 6 wells to be completely submerged in culture media. Control and experimental wells were set up as shown in FIG. 12A. For $H_2O_2$ positive controls, 9.8 M $H_2O_2$ solution (Sigma) was diluted in cell culture grade $H_2O$ (Gibco) to 10 mM stock and further diluted to working concentrations in culture media. Cells were then incubated up to 72 hours without media change and counted every 24 hours. For cell counting, a 4×4 grid on the plate cover was used for consistent counting fields. Cell strainers containing hydrogels and conditioned media were removed and replaced by Calcein-AM (1 μg/ml, Invitrogen) dissolved in phosphate-buffered saline (PBS, Gibco), followed by 10 mins incubation at 37° C. Staining solution was then replaced by PBS and the cells were imaged on an Olympus inverted fluorescence microscope with 4× objective and FITC filter set. Following imaging, conditioned media and strainer containing hydrogels were replaced and the cells were returned to the incubator. Cells were maintained at 37° C. in a 5% $CO_2$ incubator. Live cells positively stained by Calcein-AM were counted using FIJI (NIH) and averaged over 4 counting fields per well at each time point (FIG. 12). For each image, only the green channel was analyzed. Sizing thresholds were set specific to each sample with the aim of accurately counting each individual cell, resulting in threshold ranges from (0-60) to (0-170) for melanoma B16F10 cells and from (0-40) to (0-120) for breast cancer E0771 cells. The images were then transformed into a binary image with the watershed property applied, producing an image with a black background and white cells. Using "Analyze Particles," the distinct white areas from size 20 (to exclude small artifacts and debris) to size infinity were counted. Cell counts were then compiled and analyzed in Microsoft Excel.

Tumor Cell Lines

Use of tumor cell lines has been approved by the Institutional Animal Care and Use Committee (IACUC) at the University of Illinois at Urbana-Champaign, adhering to guidelines and regulations from National Institutes of Health (NIH) and US Department of Agriculture.

Figure 3B:
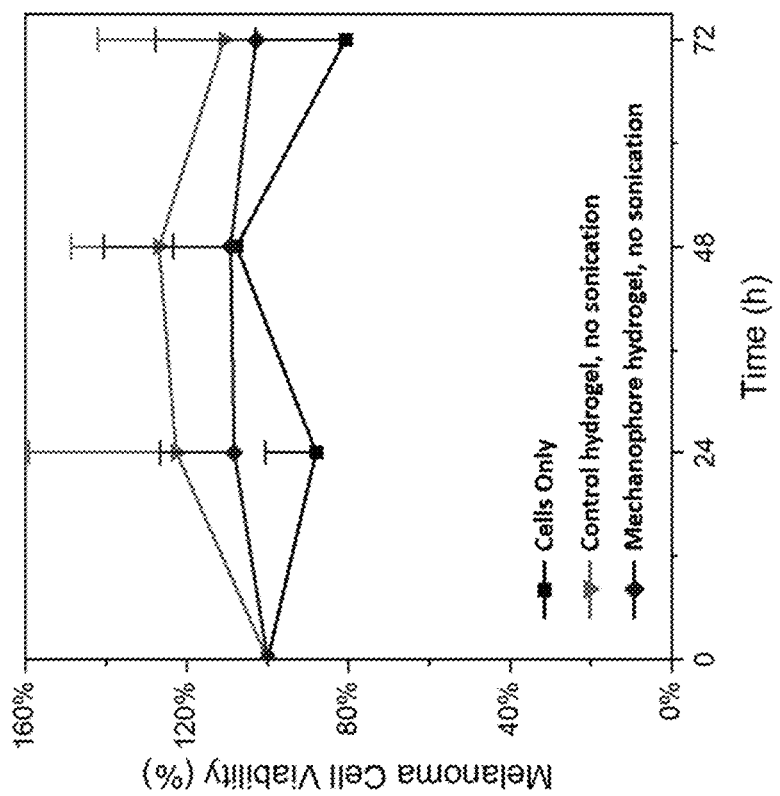
FIGS. 3A-3B show mechanochemical dynamic therapy (MDT) exhibits a mechanical not thermal effect.
Figure 3A:
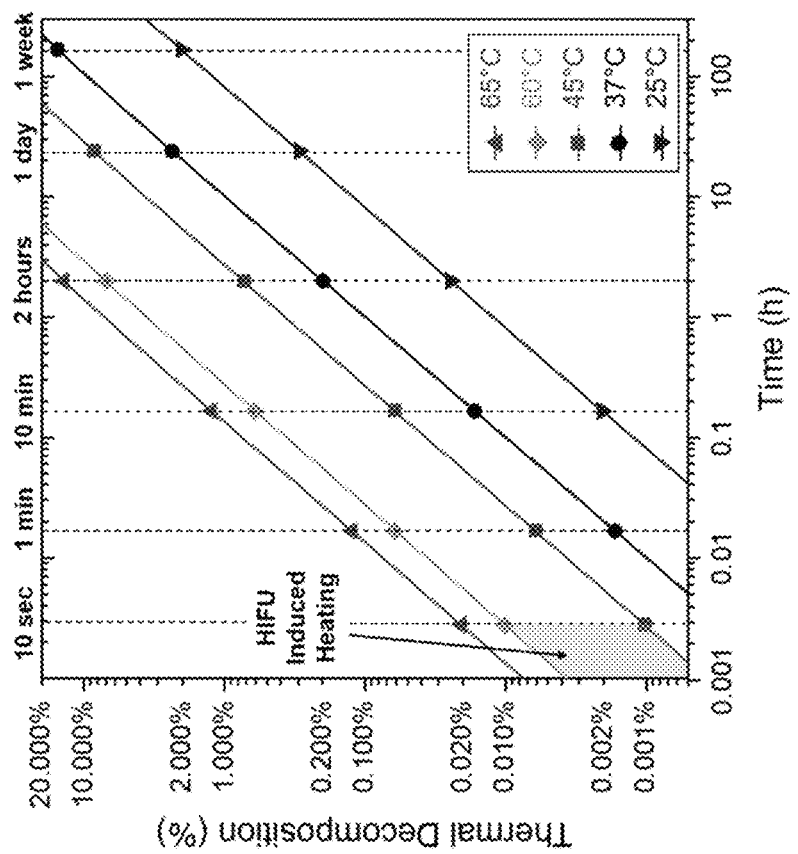

Example 1 Synthesis and Cytotoxicity Study of Azo-Mechanophore-Embedded Peg Hydrogels The concept of MDT is outlined in FIG. 1. PEG hydrogels embedded with azo-mechanophores were synthesized from azo-PEG copolymer macroinitiator and PEG diacrylate crosslinker. Upon curing at high temperature, ~14% of the azo groups thermally decomposed into FRs (FIG. 2A and Table 1), allowing the addition of the crosslinker into the hydrogel networks (FIG. 6). The majority (~86%) of azo groups did not thermally decompose and thus were incorporated into the hydrogel network as mechanophores for on demand FR generation (FIG. 2A and FIG. 7). This synthetic strategy avoids the use of toxic chemicals and is potentially suitable for scalable, low-cost production. As a control, hydrogels without mechanophores were prepared similarly by polymerizing the PEG diacrylate crosslinkers with a small molecular azo initiator, the potassium salt of 4,4'-azobis (4-cyanovaleric acid) (ACVA). Afterwards, unreacted ACVA was removed during purification. As evidence that MDT is a mechanical rather than thermal effect, we determined that the azo-mechanophores exhibit good thermal stability, with a very low (~2%/day) background decomposition rate at the physiological temperature of 37° C. (FIG. 3A and Table 1). Moreover, thermally decomposed azo-mechanophores are unlikely to generate reactive FRs, given the propensity of thermally-induced FR pairs to recombine into non-toxic products. In contrast, mechanically generated FR pairs do not recombine since they are pulled apart upon generation. The non-activated mechanophore hydrogels demonstrated no in vitro cytotoxicity under physiological conditions over at least 72 hours for both mouse melanoma (FIG. 3B) and breast cancer cells. Both mechanophore-embedded hydrogel and control hydrogel provide a better condition for culturing melanoma (FIG. 3B) and breast cancer cells than the cell only, without sonicate. The therapeutic effect of ROS from mechanophore is described in FIG. 5 and FIG. 10. The azo-mechanophores were also stable for long-term storage (decomposition: <2%/year at 4° C.), and capable of temporary ambient storage (decomposition: ~0.3%/day at 25° C.).

Figure 10A:
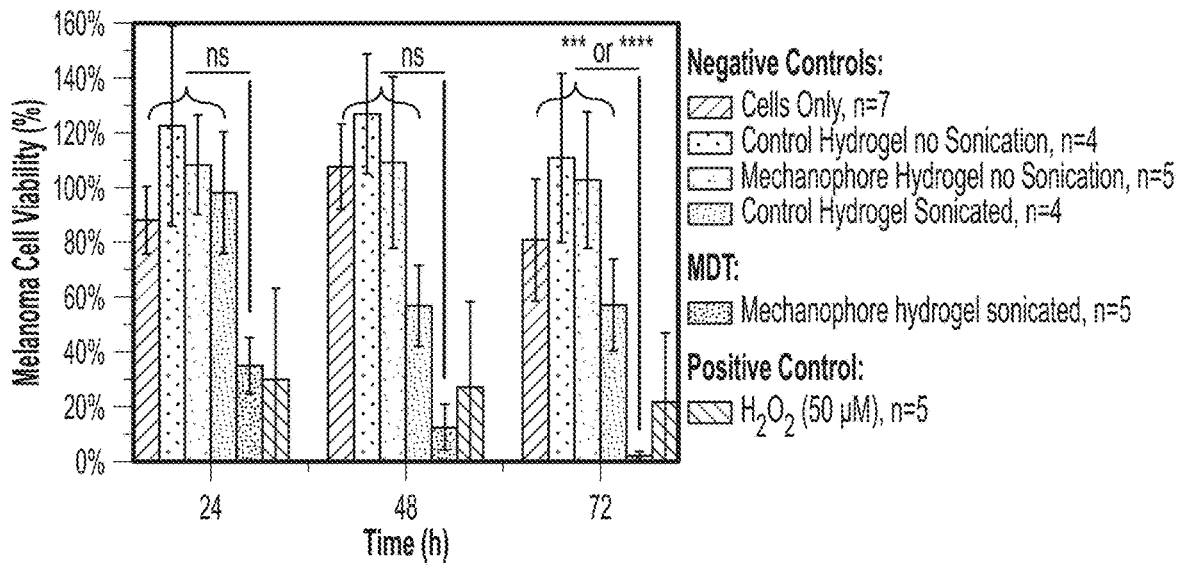
FIGS. 10A-10B show summarized cell-viability of in vitro MDT and all controls for (FIG. 10A) B16F10 melanoma cells and (FIG. 10B) E0771 breast cancer cells (ns: statistically non-significant).
Figure 10B:
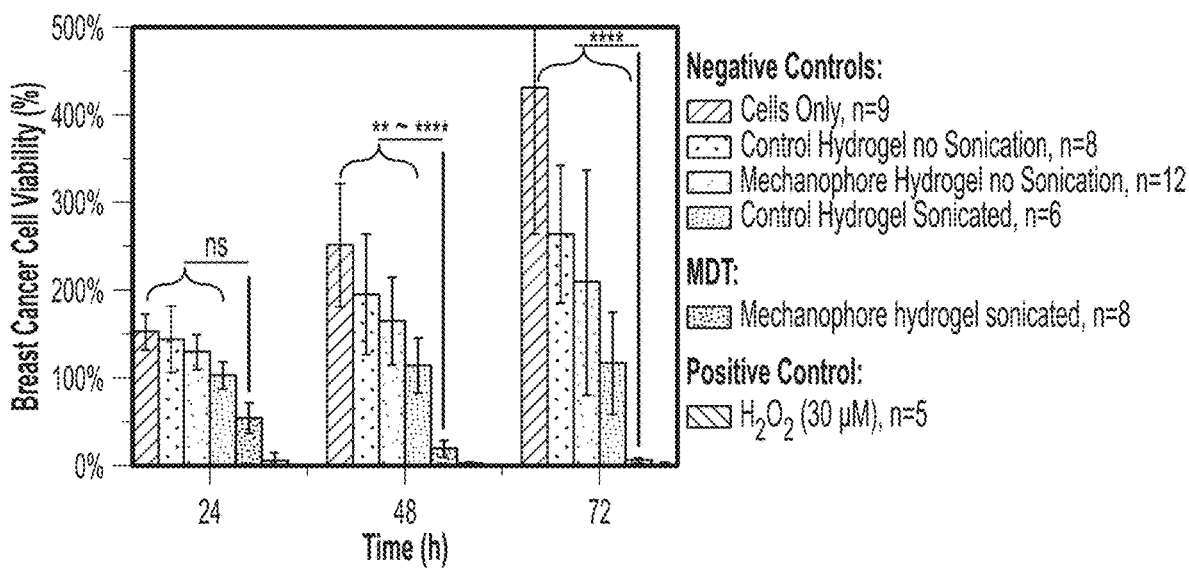

Example 2 Mechanical Activation of Azo-Mechanophore Using HIFU and Detection of ROS A HIFU-based triggering system was developed to remotely control the activation of azo-mechanophores (FIG. 2B and FIG. 8). For the irradiation, continuous-wave (CW) ultrasound at a frequency of 550 kHz was employed with a fixed sonication period (10 s-on, 20 s-off, 4 repetitions per spot) and a spatial-peak temporal average intensity ($I_{SPTA}$) of the ultrasonic beam (115 W·cm$^{-2}$, ~1.9 MPa of peak acoustic pressure amplitude). The focal spot where the ultrasonic beams was located inside the mechanophore hydrogels as shown in FIG. 2B. The lateral location of focal spots was shifted five times to guarantee high efficiency of azo-mechanophore activation. Because the azo-mechanophores are responsive to both mechanical forces and heat, we first examined local heating around the focal region induced by the irradiation of mechanophore hydrogel with HIFU. The results of this experiment distinguish a mechanical from a thermal activation stimulus. We have previously validated the high efficiency of CW ultrasound on spatiotemporal control of mechanical energy delivery for mechanophore activation (e.g., color change and light emission), while the thermal effect on mechanophore activation was insignificant. To further understand this, we monitored the temperature elevation due to the designed HIFU sonication using both a thermal infrared camera (FLIR SC620) and a thermocouple (FIG. 10). During HIFU operation at the selected intensity and period, the surface temperature of mechanophore hydrogels was monitored with the thermal infrared camera and the internal temperature elevation around the focal spot was tracked with a thermocouple. We observed a temperature gradient along the depth, i.e., an averaged peak temperature of ~41.5±0.3° C. was recorded on the surface while the temperature recorded at the focal spot was ~53.1±3.1° C., suggesting that the transmitted ultrasonic energy required for the mechanophore activation was well localized at the focal spot. Furthermore, according to the thermal decomposition kinetics shown in FIG. 3A, while temperature elevation greater than 53° C. by CW-HIFU sonication does thermally activate mechanophores within the focal spot, the decomposition percentage is less than 0.01%, combining for a mere total of <0.2% decomposition over the full 5-spot sonication regime (FIG. 9). Therefore, these results confirmed that the thermal effect was negligible and the azo-mechanophore activation was triggered by mechanical force, i.e., an acoustic radiation force. We then examined the ability of the HIFU setup to generate FRs via azo-mechanophore activation. Mechanophore hydrogels were subjected to five different sonication spots with fixed intensity (115 W·cm$^{-2}$) and four cycles, as shown in FIG. 2. We verified that the designed HIFU conditions provided a strong effect for activating azo-mechanophores, facilitating the generation of FRs.

Distinct from thermally generated FRs, mechanically generated FRs were rapidly separated to prevent recombination. Therefore, these mechano-FRs are efficiently converted into various types of ROS including $H_2O_2$. To validate the formation of ROS, luminol chemiluminescence and xylenol orange (XO)/$Fe^{2+}$ colorimetric tests were performed, as shown in FIG. 2D and FIG. 4. During luminol tests, blue chemiluminescence was clearly observed for sonicated mechanophore hydrogels, lasting for at least several minutes (FIG. 4A), confirming the formation of highly reactive ROS that oxidizes luminol for light emission. In contrast, light emission was barely observable in control studies (FIG. 4B, C). The colorimetric study was based on the oxidation of $Fe^{2+}$ into $Fe^{3+}$ that forms a purple complex with XO. The sonicated mechanophore hydrogel resulted in a faster color change (<30 min) than control materials (FIG. 4). However, $Fe^{2+}$ is not selective for highly reactive ROS— under prolonged reaction time $Fe^{2+}$ ions were oxidized by other oxidants, such as thermally stable peroxides formed during hydrogel synthesis that remained covalently bound to the polymer network (FIG. 7). These stable peroxides did not impart cytotoxicity and were not active for MDT treatment, but their presence did affect the ROS quantification in this colorimetric assay.

Example 3: Cytotoxicity of Mouse Cancer Cells by MDT: Melanoma (B16F10)

Figure 5A:
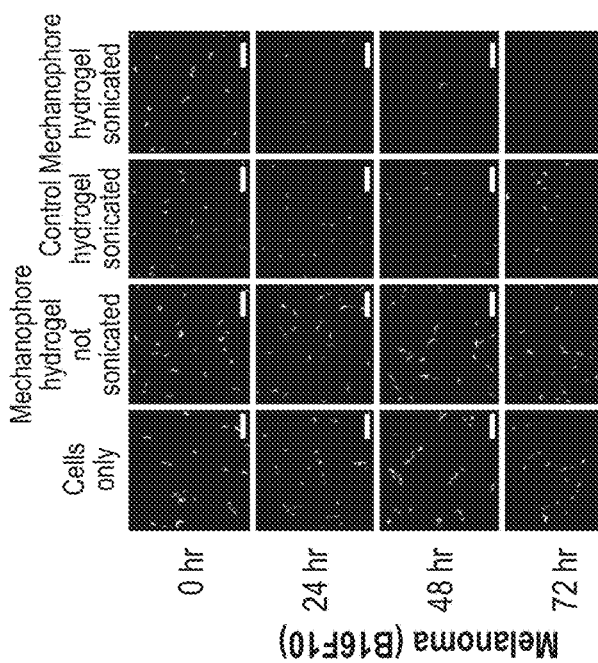
FIGS. 5A-5D show Fluorescence images and quantification of live tumor cells before (0 h) and after (24-72 h) MDT (sonicated control and mechanophore hydrogel) compared to controls (cells only and non-sonicated mechanophore hydrogel) for melanoma (FIG. 5A, FIG. 5B) and breast cancer (FIG. 5C, FIG. 5D). Scale bar: 250 µm; ns: statistically non-significant.
Figure 5B:
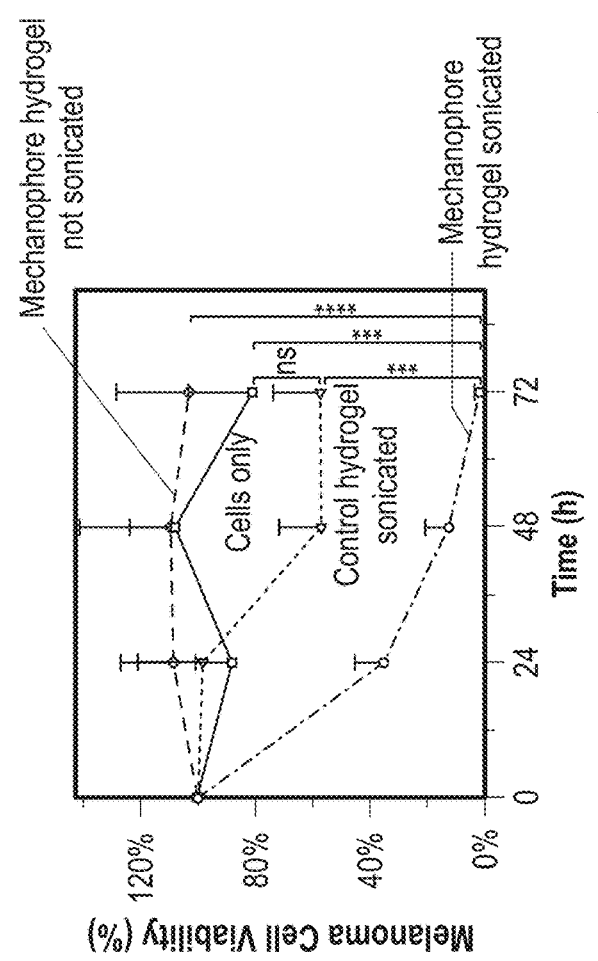
Figure 13:
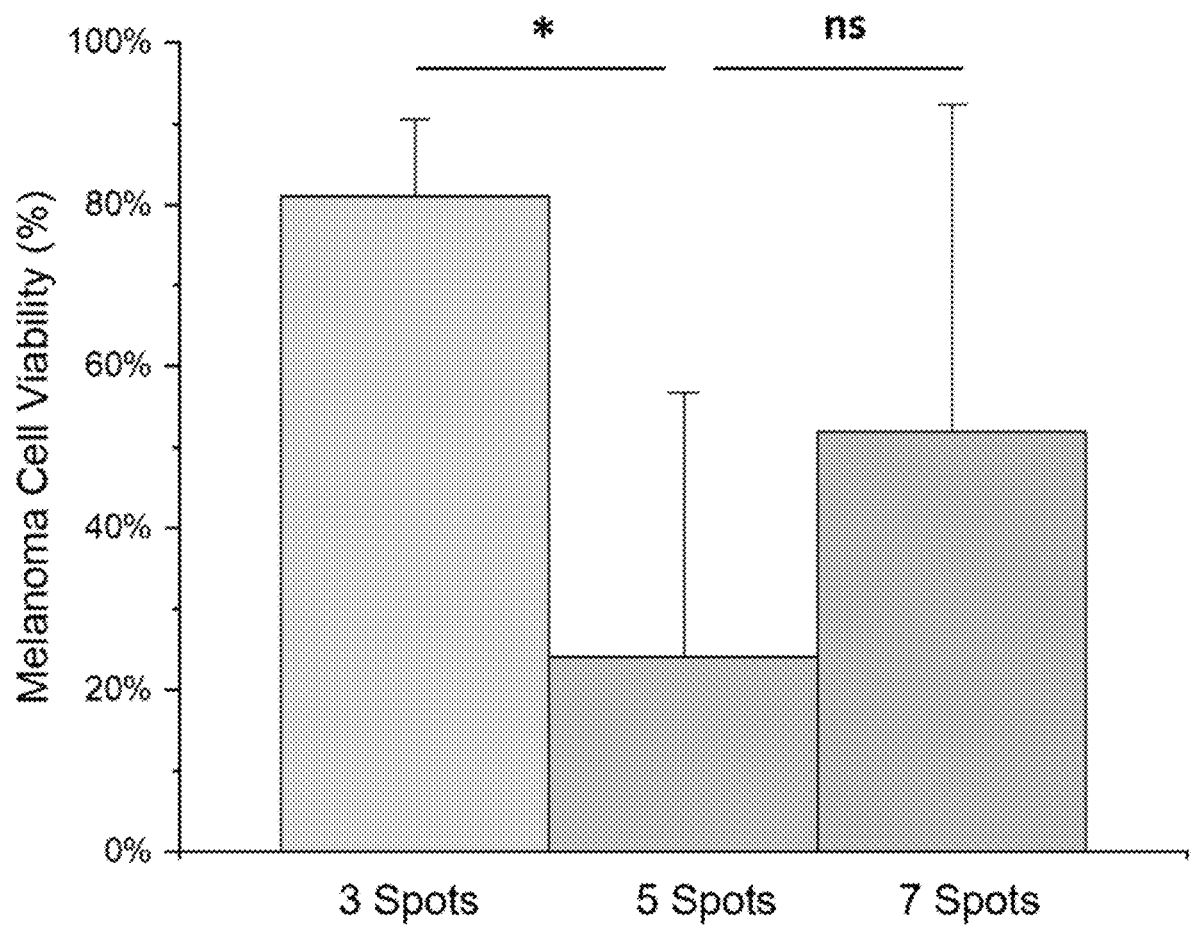
FIG. 13 shows Melanoma cell viability measured 24 hours after in vitro MDT with 3, 5 or 7 spots of sonication (n=3).

To examine the therapeutic potential of the azo-mechanophores for ROS generation, we performed in vitro challenge assays in the B16F10 murine skin melanoma cancer model. B16F10 is an aggressive metastatic form of mouse skin melanoma widely used in cancer studies. For MDT, the mechanophore hydrogels were activated and exposed to the cancer cells for 72 hours via the established CW-HIFU sonication procedure. The number of sonication spots (5 spots) was determined after the validation of the therapeutic efficacy of ROS on cytotoxicity (FIG. 13). Upon exposure to activated hydrogels, viable B16F10 cell population positive for Calcein-AM fluorescence decreased over the course of 72 hours in a sonication spot number-dependent manner. The number of live cells that exhibit Calcein-AM fluorescence were counted every 24 hours using the FIJI software as detailed in the SI. As shown in FIG. 5A, the number of live B16F10 tumor cells decreased significantly over 72 hours after MDT, with the death rate close to 100% (FIG. 5B). In comparison, neither sonicated non-mechanophore hydrogels, nor non-sonicated mechanophore hydrogels, imparted statistically significant influence on melanoma cell population over 72 hours, demonstrating that both mechanophore and sonication are necessary for MDT. The overall effectiveness of MDT was comparable to the positive control experiment—a challenge by a lethal dosage of $H_2O_2$ of ~50 μM (FIG. 10), demonstrating the potency of cell killing from ROS generation by the activated mechanophores. As an estimation, complete conversion of all azo-mechanophores within the focal spots would produce ~500 μM of $H_2O_2$ (43); therefore, approximately 10% of the azo-mechanophores were effectively activated during MDT.

Example 4: Cytotoxicity of Mouse Cancer Cells by MDT: Breast Cancer Model (E0771)

Figure 5C:
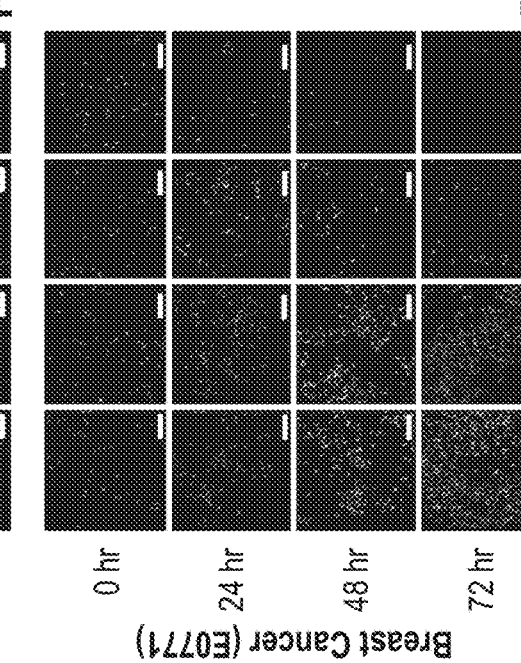
Figure 5D:
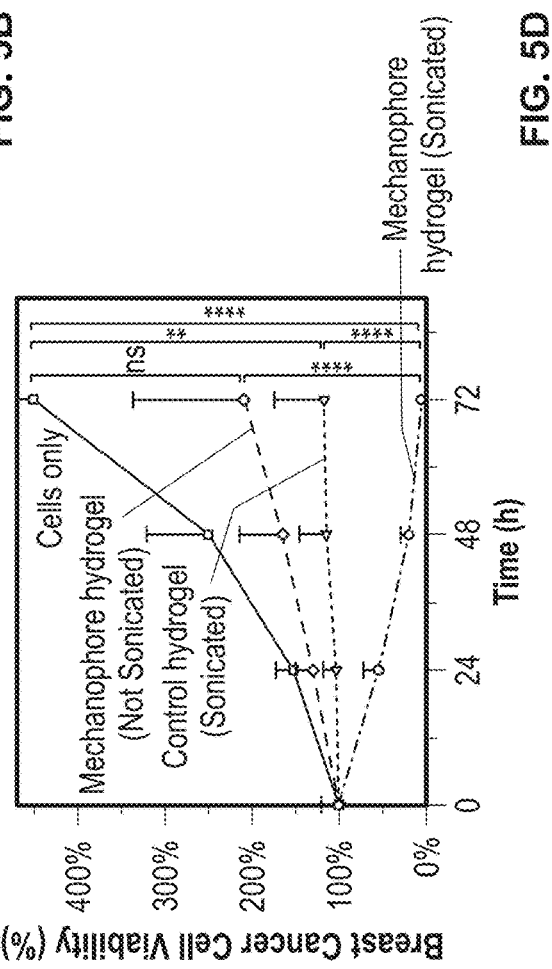

In addition to B16F10, we tested the therapeutic potential of the azo-mechanophores in the E0771 murine breast cancer cell line in vitro. E0771 is a well-studied mouse breast cancer model that is strongly proliferative, aggressive and highly metastatic. Mechanophore hydrogels were activated via the established CS-HIFU sonication procedure. Upon exposure to the activated hydrogels, viable E0771 cells positive for Calcein-AM fluorescence were counted every 24 hours for 72 hours. As shown in FIG. 5C, the population of E0771 tumor cells decreased significantly over 72 hours, while untreated control cells proliferated over 400%. The death rate of the MDT treated cells was close to 100% (FIG. 5D). For sonicated non-mechanophore control hydrogels, modest reduction of cell proliferation was observed; however, the amount of tumor cells did not decrease significantly, and the inhibition was not sufficient for effective treatment. In the absence of mechanophores, ultrasound can still break the conventional covalent bonds in the polymer backbone of the hydrogels, which also generates free radicals and ROS. Compared to activating a mechanophore, however, breaking conventional covalent bonds requires much higher mechanical force. Therefore, the amount of ROS formed by non-mechanophore hydrogels were much lower. The ROS generated from non-mechanophore may account for the slight inhibitory effect observed from the sonicated non-mechanophore hydrogels, which is insufficient for effective cancer treatment. On the other hand, non-sonicated mechanophore hydrogels resulted in non-statistically significant cell death, which was consistent with the non-cytotoxicity of non-activated mechanophore hydrogels. The overall MDT effectiveness was comparable to the positive control—challenge by lethal dosage of $H_2O_2$ of ~30 μM (FIG. 10), again demonstrating the potency of the ROS generated by the activated mechanophores.

Example 5

Figure 14:
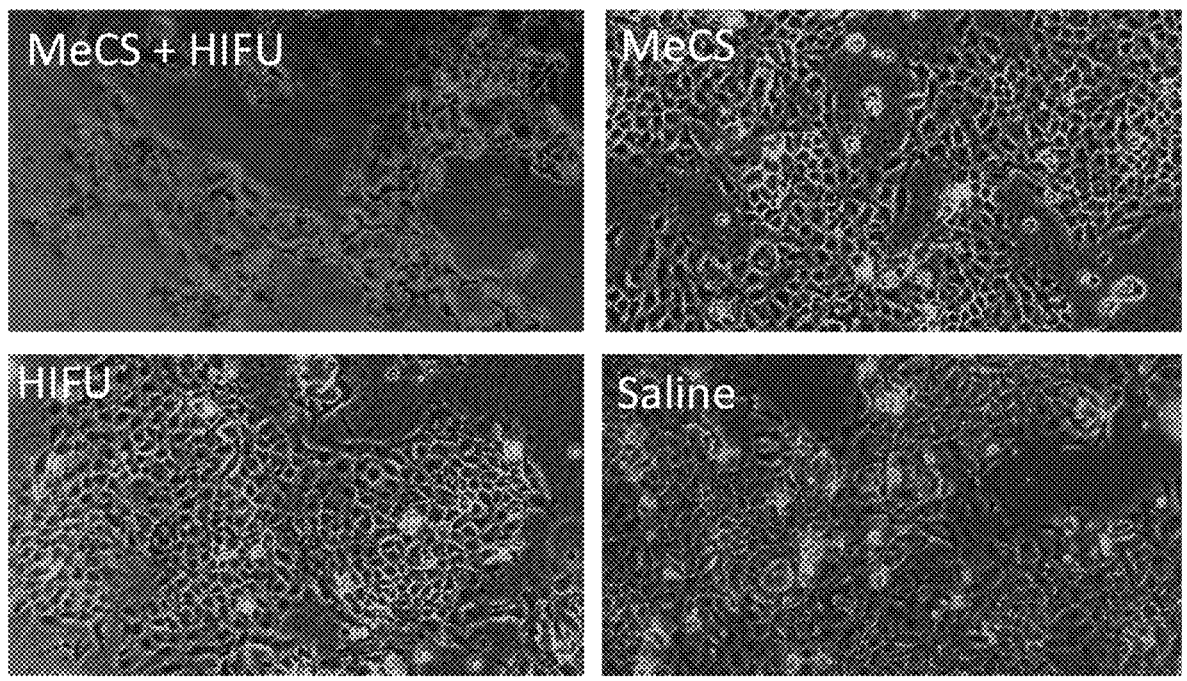
FIG. 14 shows bright field and fluorescence (blue color: DAPI) microscopic images of 4T1 cells (5E4 cells) incubated with (i) mechanophore hydrogel nanoparticles (1E6 particles/mL) and treated with focused ultrasound (FUS) (26 J/$cm^2$), (ii) mechanophore hydrogel nanoparticles only, (iii) FUS only, and (iv) saline. MeCS stands for mechanochemical sensitizers, which is an abbreviation of the mechanophore hydrogel nanoparticles.

4T1 cells (5E4 cells, breast cancer cell line) were incubated with (i) mechanophore hydrogel nanoparticles (1E6 particles/mL) and treated with focused ultrasound (FUS) (26 J/cm$^2$), (ii) mechanophore hydrogel nanoparticles only, (iii) FUS only, and (iv) saline. The cells were visualized with bright field and fluorescence (blue color: DAPI) microscopy. See FIG. 14. MeCS stands for mechano-chemical sensitizers, which is an abbreviation of the mechanophore hydrogel nanoparticles. The death rate of the cells incubated with mechanophore hydrogel nanoparticles and treated with focused ultrasound (FUS) had a very high death rate as compared to the treatment conditions.

Figure 15:
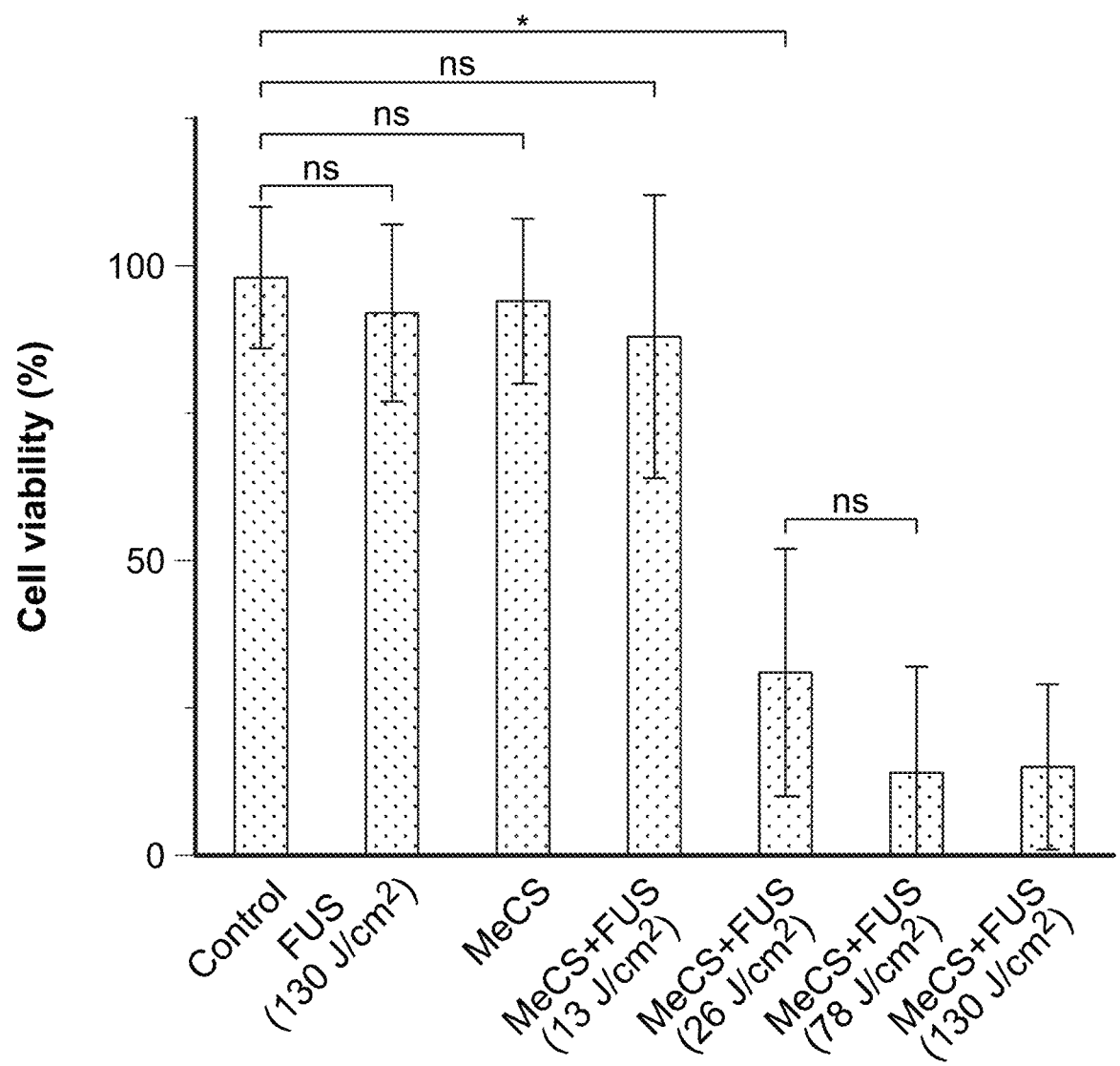
FIG. 15 shows quantitative analysis of cell viability of triple negative breast cancer cells (5E4 cells) treated with FUS, mechanophore hydrogel nanoparticles (1E6 particles/mL) only, and MDT (mechanophore hydrogel nanoparticles with various doses of FUS from 13 to 130 J/$cm^2$), n=5, *$p \leq 0.001$; ns: not statistically significant.

A quantitative analysis of cell viability of triple negative breast cancer cells (5E4 cells) treated with FUS, mechanophore hydrogel nanoparticles (1E6 particles/mL) only, and MDT (mechanophore hydrogel nanoparticles with various doses of FUS from 13 to 130 J/cm$^2$) was completed. The results are shown in FIG. 15. The treatment conditions with 26 J/cm$^2$, 78 J/cm$^2$, and 130 J/cm$^2$ showed significantly less cell viability than the control conditions and the 13 J/cm$^2$ treatment conditions.

Figure 16:
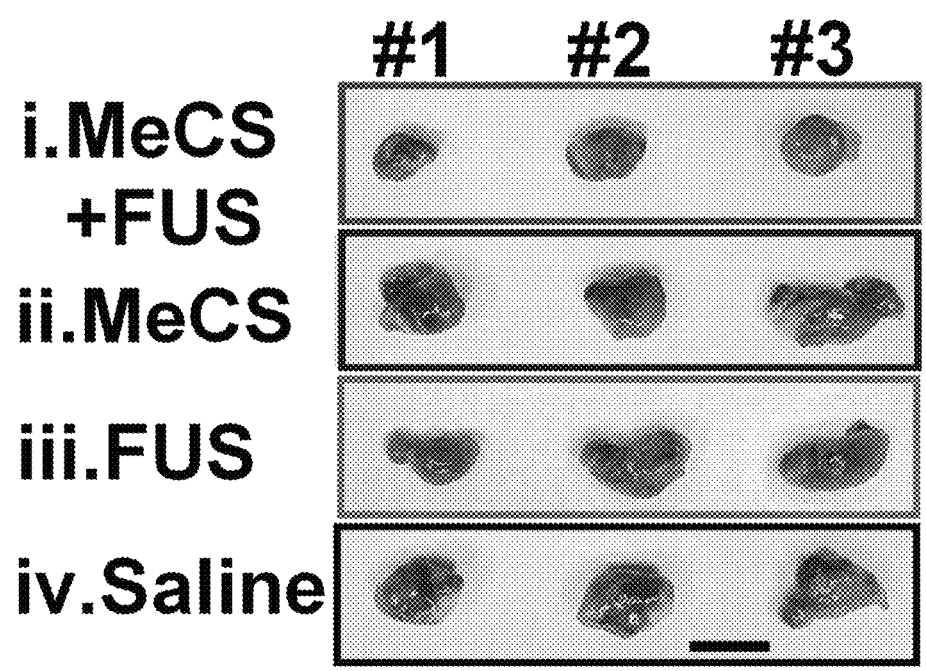
FIG. 16 shows harvested TNBC tumors after treated with MDT and various control experiments. (i) Mechanophore hydrogel nanoparticles (4E6 particles) with FUS (26 J/$cm^2$) every 2 days for 5 times, (ii) mechanophore (4E6 particles) without FUS, and (iii) FUS (26 J/$cm^2$) every 2 days for 5 times, and (vi) saline without FUS.
Figures 17A, 17B:
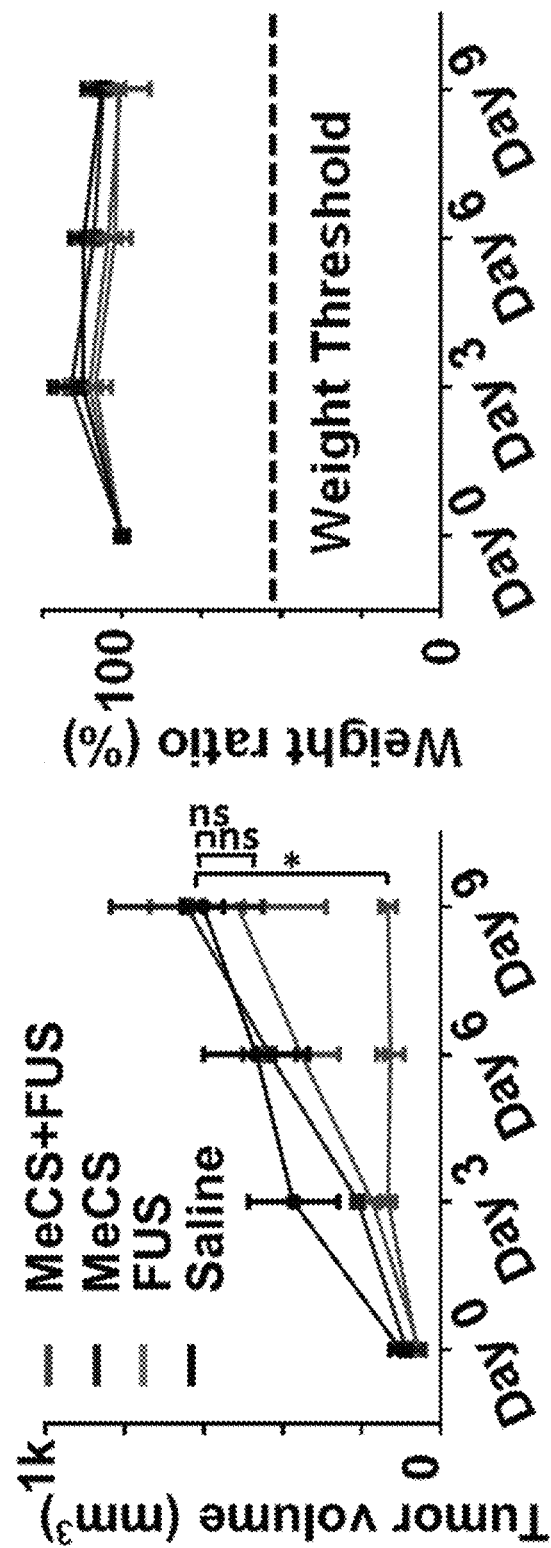
FIGS. 17A-17B show (17A) the tumor growth curve of the four groups of mice (n=3) treated with methods (i) to (vi). 16. ns: not statistically significant, *: $p<0.001$. (17B) Weight chart of the four groups of mice (n=3) treated with methods (i) to (vi). Method (i) MeCS (4E6 particles) with FUS (26 J/$cm^2$) every 2 days for 5 times, (ii) MeCS (4E6 particles) without FUS, and (iii) FUS (26 J/$cm^2$) every 2 days for 5 times, and (vi) saline without FUS.

Harvested TNBC tumors were treated with MDT and various control conditions. (i) mechanophore hydrogel nanoparticles (4E6 particles) with FUS (26 J/cm$^2$) every 2 days for 5 times, (ii) mechanophore (4E6 particles) without FUS, and (iii) FUS (26 J/cm$^2$) every 2 days for 5 times, and (vi) saline without FUS. The tumors are shown in FIG. 16. The tumors treated with mechanophore hydrogel nanoparticles combined with FUS were significantly smaller than the other tumors. The tumor growth curve of the four groups of mice (n=3) treated with methods (i) to (vi) is shown in FIG. 17*a*. The mechanophore hydrogel nanoparticles (4E6 particles) with FUS (26 J/cm$^2$) treatment group had significantly lower tumor volume. The weight chart of the four groups of mice (n=3) treated with methods (i) to (vi) is shown in FIG. 17*b*.

Figure 18:
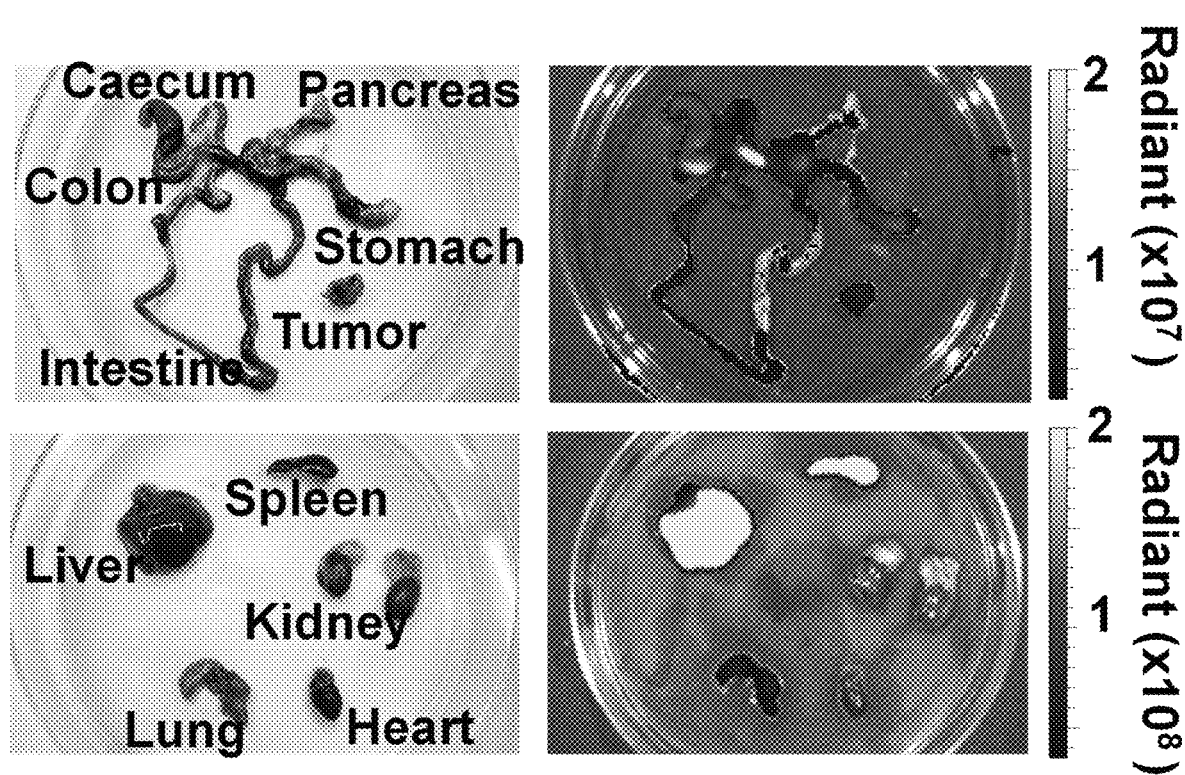
FIG. 18 shows the biodistribution of mechanophore hydrogel nanoparticles (MeCS) in a 4T1 tumor-bearing mouse (3 hours after injection). The fluorescence/bright field image shows the harvested main organs from one mouse intravenously injected with the nanoparticles (5E9 particles). The fluorescence signal indicates Cy7 dyes in the nanoparticles.
Figure 19:
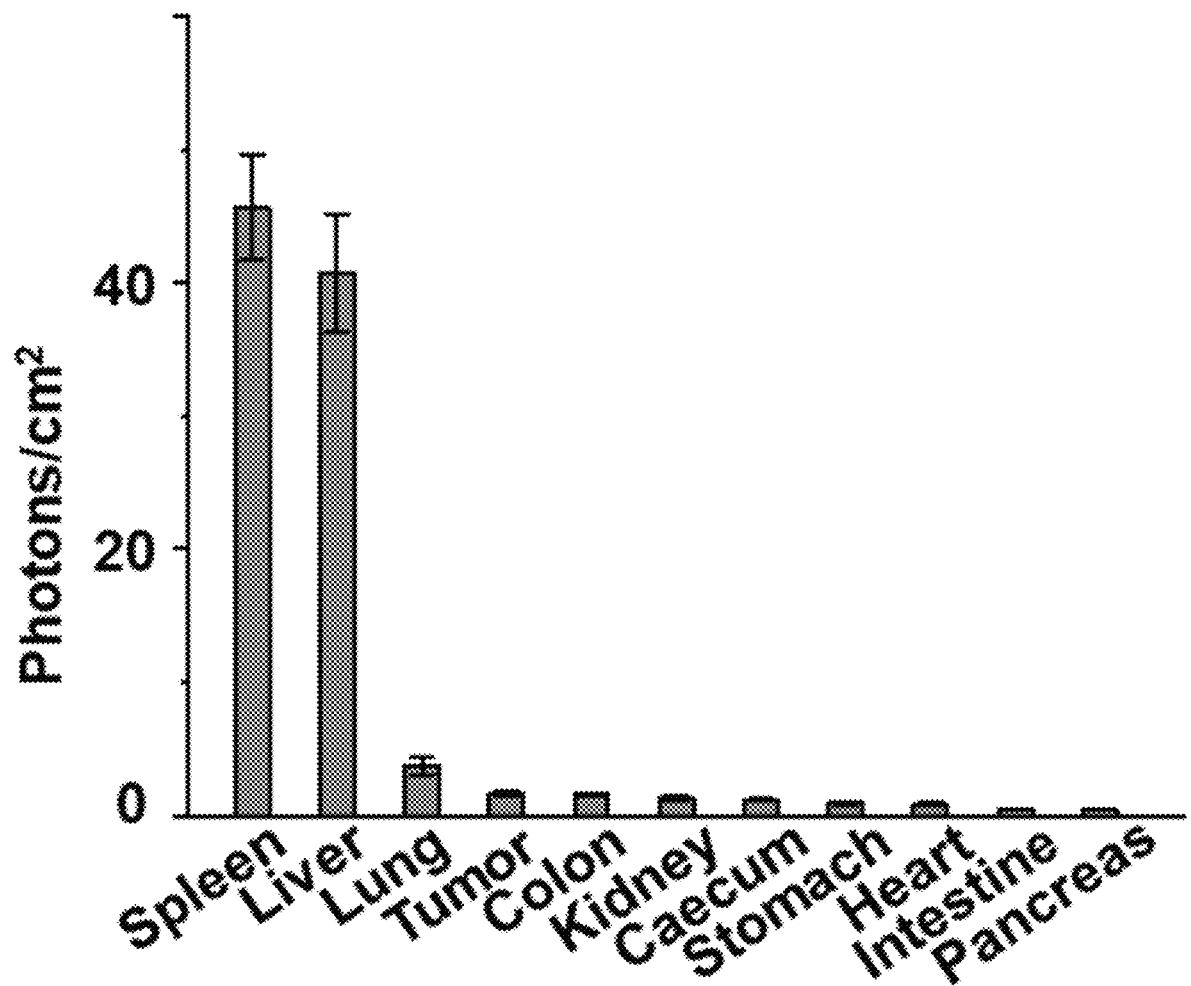
FIG. 19 shows a quantitative analysis of biodistribution and tumor-to-organ ratios of the mechanophore hydrogel nanoparticles (MeCS). The nanoparticles are mainly accumulated in the liver and spleen 3 hours after injection. The tumor-to-spleen ratio of nanoparticle accumulation is 1:28.5, indicating the EPR accumulation. n=6, *: $p=0.22$; **: $p<0.00001$.

The biodistribution of mechanophore hydrogel nanoparticles (MeCS) in a 4T1 tumor bearing mouse (3 hours after injection) was examined by the fluorescence/bright field image. See FIG. 18, which shows the harvested main organs from one mouse intravenously injected with the nanoparticles (5E9 particles). Fluorescence signal indicates Cy7 dyes in the nanoparticles. The quantitative analysis of biodistribution and tumor to organ ratios of the mechanophore hydrogel nanoparticles (MeCS) is shown in FIG. 19. The nanoparticles are mainly accumulated in liver and spleen 3 hours after injection. The tumor to spleen ratio of nanoparticle accumulation is 1:28.5, indicating the EPR accumulation. n=6, *: p=0.22; **: p<0.00001.

Example 5: Conclusion

In summary, we provided the first demonstration that ROS-generating mechanophores in hydrogels are of interest in a biomedical context, particularly I for noninvasive cancer therapy. Using exemplary azo-mechanophores in a biocompatible PEG hydrogel coupled with HIFU, we developed a new cancer therapy platform, mechanochemical dynamic therapy (MDT), enabling the targeted release of ROS. The non-activated azo-mechanophore hydrogels resulted in no cytotoxicity due to good thermostability; while upon HIFU sonication, they rapidly generate reactive FRs and ROS to kill tumor cells in a non-invasive manner. With these advances, MDT achieves therapeutic efficacy of ~100% within 72 hours in in vitro tumor models including melanoma (B16F10) and breast cancer models (E0771), which is comparable to a lethal dosage (30-50 μM) of $H_2O_2$. As a control, HIFU sonication of hydrogels without mechanophores produced limited amounts of ROS and were ineffective for effective treatment. Furthermore, evidence was provided to show that mechanophores role in MDT result from the formation of ROS. Therefore, biocompatible hydrogels embedded with mechanophores are new members of the therapeutic biomaterial family. Conditions for HIFU sonication (e.g., intensity, penetration depth, etc.) and mechanophore activation (e.g., bond cleavage threshold, etc.) are tunable. Therefore, the MDT method can be used in in vivo models and clinical applications including non-superficial glioblastoma, pancreatic cancer, etc. Some examples of therapeutic uses include, inter alia, (1) direct intra-tumoral injection of biocompatible hydrogels where azo-mechanophore are embedded; and (2) systematic injection of tumor-homing mechanophore-loaded nanocarriers. After successful development of both candidates, remote triggering of mechanophores via image-guided HIFU will facilitate spatiotemporally precise release of ROS at the tumor site. These approaches will not only provide new insights into target drug delivery via mechanical triggering of mechanophores, but also open the door for exploiting polymer mechanochemistry for clinical purposes. Together with existing imaging modalities like ultrasound and MRI for image guidance, MDT will provide a new framework for cancer therapy.

We claim:

1. A method of generating reactive oxygen species comprising contacting a composition comprising one or more azo-mechanophores covalently linked to a hydrogel matrix or biodegradable elastomer matrix wherein the one or more azo-mechanophores are present in the hydrogel matrix or biodegradable elastomer matrix at about 3.0 wt % to about 15 wt % with high intensity focused ultrasound (HIFU).

2. A method of killing cells, tissue, or tumors comprising delivering a composition comprising one or more azo-mechanophores covalently linked to a hydrogel matrix or biodegradable elastomer matrix wherein the one or more azo-mechanophores are present in the hydrogel matrix or biodegradable elastomer matrix at about 3.0 wt % to about 15 wt % to the cells, tissue, or tumors and activating the azo-mechanophores with HIFU.

3. The method of claim 2, wherein the cells, tissue, or tumors are cancerous and are present in a mammal.

4. The method of claim 2, wherein the cells, tissue, or tumors are present in vitro.

5. The method of claim 2, wherein the HIFU penetrates into the cells, tissue, or tumors to a depth of more than 1 cm.

6. The method of claim 2, wherein the HIFU delivers continuous wave ultrasound in a pulse, wherein the pulse can be delivered once, twice, or by repeated pulsing.

7. The method of claim 3, further comprising delivering one or more additional cancer therapies to the mammal.

8. A method of killing cells, tissue, or tumors comprising delivering a composition comprising:
  (i) one or more azo-mechanophores and a nanocarrier wherein the azo-mechanophores comprise about 3.0 wt % to about 15 wt % of the composition; or
  (ii) one or more azo-mechanophores a nanocarrier, and one or more tumor-homing compounds, wherein the azo-mechanophores comprise about 3.0 wt % to about 15 wt % of the composition;
  wherein the composition does not comprise a chemotherapeutic agent other than the one or more azo-mechanophores,
  to the cells, tissue, or tumors and activating the azo-mechanophores with HIFU.

9. The method of claim 8, wherein the cells, tissue, or tumors are cancerous and are present in a mammal.

10. The method of claim 8, wherein the cells, tissue, or tumors are present in vitro.

11. The method of claim 8, wherein the HIFU penetrates into the cells, tissue, or tumors to a depth of more than 1 cm.

12. The method of claim 8, wherein the HIFU delivers continuous wave ultrasound in a pulse, wherein the pulse can be delivered once, twice, or by repeated pulsing.

13. The method of claim 3, further comprising delivering one or more additional cancer therapies to the mammal.

14. The method of claim 1, wherein the hydrogel matrix or biodegradable elastomer matrix has a diameter or width of about 0.5 μM to about 10 mm.

15. The method of claim 1, wherein the hydrogel matrix comprises polydimethylsiloxane (PDMS) or polyethylene glycol (PEG).

16. A method of killing cells, tissue, or tumors comprising delivering a composition consisting of:

(i) one or more azo-mechanophores, peroxide-mechanophores, or disulfide-mechanophores and a nanocarrier wherein the azo-mechanophores comprise about 3.0 wt % to about 15 wt % of the composition; or (ii) one or more azo-mechanophores a nanocarrier, and one or more tumor-homing compounds, wherein the azo-mechanophores comprise about 3.0 wt % to about 15 wt % of the composition;

to the cells, tissue, or tumors and activating the azo-mechanophores with HIFU.

17. The method of claim 16, wherein the cells, tissue, or tumors are cancerous and are present in a mammal.

18. The method of claim 16, wherein the azo-mechanophores mechanically generate free radicals when subjected to the HIFU, which are converted to reactive oxygen species.

19. The method of claim 16, wherein the reactive oxygen species kill the cells, tissue, or tumors via oxidative cytotoxicity, apoptosis, or both.

20. The method of claim 16, wherein the HIFU penetrates into the cells, tissue, or tumors to a depth of more than 1 cm.

* * * * *